(12) United States Patent
Rasekhi

(10) Patent No.: US 8,196,850 B2
(45) Date of Patent: *Jun. 12, 2012

(54) SELF-CLEARING RASP SYSTEM FOR AUTOMATIC MILLING APPARATUS

(76) Inventor: Houshang Rasekhi, Sandy, UT (US)

( * ) Notice: Subject to any disclaimer, the term of this patent is extended or adjusted under 35 U.S.C. 154(b) by 239 days.

This patent is subject to a terminal disclaimer.

(21) Appl. No.: 12/559,048

(22) Filed: Sep. 14, 2009

(65) Prior Publication Data

US 2010/0004653 A1    Jan. 7, 2010

Related U.S. Application Data

(63) Continuation-in-part of application No. 11/623,623, filed on Jan. 16, 2007, now Pat. No. 7,588,202.

(60) Provisional application No. 61/206,010, filed on Jan. 27, 2009, provisional application No. 61/198,491, filed on Nov. 7, 2008, provisional application No. 60/759,475, filed on Jan. 17, 2006, provisional application No. 60/812,867, filed on Jun. 12, 2006.

(51) Int. Cl.
*B02C 18/16* (2006.01)

(52) U.S. Cl. .......... 241/94; 241/100; 241/224; 241/262; 241/606

(58) Field of Classification Search .................... 241/92, 241/100, 224, 262, 606, 94
See application file for complete search history.

(56) References Cited

U.S. PATENT DOCUMENTS

| | | | |
|---|---|---|---|
| 2,583,595 A | 1/1952 | Rodel et al. | |
| 2,761,627 A | 9/1956 | Reed | |
| 3,528,617 A | 9/1970 | Trevathan | |
| 4,101,082 A | 7/1978 | Mayer et al. | |
| 4,216,919 A | 8/1980 | Trevathan | |
| 4,252,282 A | 2/1981 | Vermeulen et al. | |
| 4,469,283 A | 9/1984 | Noguchi et al. | |
| 5,048,764 A | 9/1991 | Flament | |
| 5,062,576 A | 11/1991 | Burda | |
| 5,201,475 A | 4/1993 | Nakagomi | |
| 5,487,509 A | 1/1996 | Hama | |
| 5,683,406 A | 11/1997 | Altobelli et al. | |
| 5,769,853 A | 6/1998 | Quétin | |
| 5,810,472 A | 9/1998 | Penaranda et al. | |
| 5,817,097 A | 10/1998 | Howard et al. | |
| 5,906,322 A | 5/1999 | Hama | |
| 5,918,821 A | 7/1999 | Grooms et al. | |
| 6,109,551 A | 8/2000 | Sullivan | |
| 6,287,312 B1 | 9/2001 | Clokie et al. | |
| 6,318,651 B1 | 11/2001 | Spiering | |

(Continued)

OTHER PUBLICATIONS

Office Action mailed Dec. 26, 2008 for U.S. Appl. No. 11/623,623.

*Primary Examiner* — Mark Rosenbaum
(74) *Attorney, Agent, or Firm* — Austin Rapp & Hardman

(57) ABSTRACT

Two self-clearing radial rasp systems for automatic milling material disclosed. In addition, as examples two automatic apparatuses utilizing said rasp systems for milling material disclosed. The rasp system may include a rasp and a trimming member. The radial rasp may include a base surface that may include cutting teeth with apertures of predetermined sizes disposed adjacent the cutting teeth. The revolving radial trimming member may include radial channels which may independently partitioned for confining and directing material toward the base surface of the rasp as the material move by centrifugal force in a radial direction. The rasp may have different sizes of cutting teeth associating with the individual radial channels of the radial trimming member.

13 Claims, 24 Drawing Sheets

U.S. PATENT DOCUMENTS

| | | |
|---|---|---|
| 6,402,070 B1 | 6/2002 | Ishida et al. |
| 6,484,954 B2 | 11/2002 | Lenox |
| 6,755,365 B1 | 6/2004 | Meredith |
| RE38,630 E | 10/2004 | Lazzara et al. |
| 6,824,087 B2 | 11/2004 | McPherson et al. |
| 7,137,581 B2 | 11/2006 | Takayama et al. |
| 7,588,202 B2 * | 9/2009 | Rasekhi ............ 241/92 |
| 2002/0040943 A1 | 4/2002 | Lenox |
| 2005/0173573 A1 | 8/2005 | Hay et al. |
| 2005/0194481 A1 | 9/2005 | Hay et al. |
| 2006/0138260 A1 | 6/2006 | Hay et al. |

\* cited by examiner

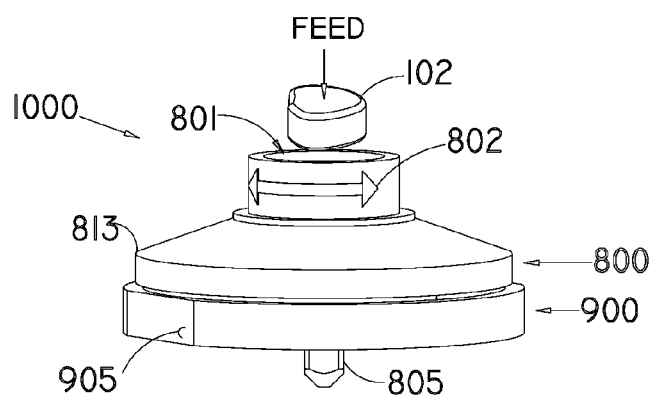
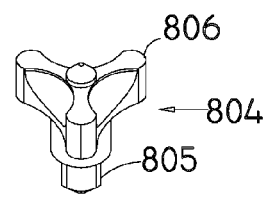
FIG. 17A
FIG. 17B
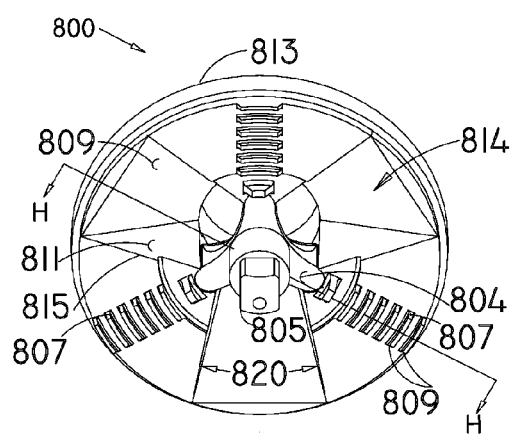
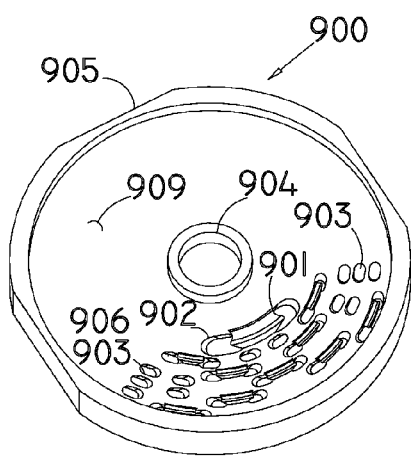
FIG. 17C
FIG. 17D

SELF-CLEARING RASP SYSTEM FOR AUTOMATIC MILLING APPARATUS

RELATED APPLICATIONS

This application is related to and claims priority to Provisional U.S. Patent Application Ser. No. 61/206,010, filed on Jan. 27, 2009, for a SELF-CLEARING RASP SYSTEM FOR AUTOMATIC MILLING APPARATUS, with inventor Houshang Rasekhi; and further claims priority to Provisional U.S. Patent Application Ser. No. 61/198,491, filed on Nov. 7, 2008, for AUTOMATIC APPARATUS FOR MILLING MATERIAL with inventor Houshang Rasekhi; and further claims priority to and is a continuation-in-part application of U.S. patent application Ser. No. 11/623,623 filed Jan. 16, 2007, for an APPARATUS FOR MILLING MATERIAL, with inventor Houshang Rasekhi; which claims priority to Provisional U.S. Patent Application Ser. No. 60/759,475, filed on Jan. 17, 2006, for a BONE MILL WITH VACUUM MIXING SYSTEM, with inventor Houshang Rasekhi and which also claims priority to Provisional U.S. Patent Application Ser. No. 60/812,867, filed Jun. 12, 2006, for BONE MILL WITH RECIPROCATING SELF-CLEANING RASP AND VACUUM MIXING SYSTEM, with inventor Houshang Rasekhi; all of which incorporated herein by this reference.

One embodiment of the present specification focuses on improvement of rasp systems for automatic milling apparatus and providing examples of apparatuses for automatic milling, particularly milling autogenic and allogenic bone for bone grafts. Furthermore, realizing that the bone mills in current use produce morselized bone that may have more uniform particle-size distribution profile that may desirable, one embodiment of this invention also focuses on providing rasp systems capable of providing morselized bone with broader particle-size distribution profile, which may have superior biomechanics, for example, when compacted in a hip or knee arthroplasty.

TECHNICAL FIELD

The present invention relates generally to milling methods and devices. More specifically, the present invention relates to apparatus for milling material, particularly automatically milling bone material.

BACKGROUND

The autograft bones (autogenous chips) harvested from the bones of the same person during the same operating procedures or allograft (living tissue transferred between two genetically different individuals of the same species), cut into smaller pieces, may create morselized bone. Morselized bone, dry or mixed with selected fluids, used as bone grafts in surgical procedures to repair or augment skeletons.

The available bone mills generally suffer from inability to produce, consistently and repeatedly, morselized bone with needed particle-size distribution profile to produce needed dense bone graft with desired biomechanics properties, within the time constrain of surgical procedures.

The available manually operated bone mills suffer from inability to produce adequate amount of morselized bone within the time constraint during the surgical procedures. Considering the cost per minute associating with the surgical hospital room and facilities, and the supporting staff, the low cost manually operated bone mills may lose their price advantage; and, indeed, may effectively be significantly expensive, instead. The manually operated bone mills may be suitable for surgical procedures requiring small amount of morselized bone.

Furthermore, the available powered bone mill apparatuses suffer from either transferring heat to the milled bone particles during the milling process that may damage the particles, or requiring an operator to attend the mill skillfully pushing the hard bone material against a rasp for producing bone particles, which may incur additional personnel costs.

For example, in the case of bone mill functioning similar to a coffee grinder, the milled particles and the material remains in the same milling chamber until the end of the milling procedure; and during the milling time, milled particles unnecessarily undergo impacts with each other and with the dull blade, generating heat energy that may damage the milled particles. Further, bone mill of coffee grinder design often fail to complete the needed milling; it creates fine, dust-like, milled bone particles with not-milled marble-like bone pieces that are beyond the mill's ability to mill. Therefore, these types of powered bone mills suffer from inability to provide morselized bone with the desired particle-size distribution profile, and having inherent problems with heating and damaging milled particles.

For another example, the powered bone mill functioning as a crusher often produces large bone slivers that may not be suitable for utilization in bone graft; under the constrained surgical time, the trained operator may have to recycle the first time-milled particles through the mill until achieving the desired finer bone particle-size distribution profile. These types of bone mills may suffer from inability to provide morselized bone with a predetermined particle-size distribution.

In some other cases, such as when the bone mill function as a powered cheese grater, a trained operator must push the bone against a rotating rasp hoping that the rasp would not clog and the operator may not face unclogging problem under time constrain during a surgical procedure. These types of bone mills often suffer from inability to provide morselized bone with the desired broad particle size distribution and requiring additional costly trained operator.

In all cases, none of the bone mills in current use may produce morselized bone with the needed particle-size distribution profile as N. T. Brewster, et al, discovered through their research (Mechanical consideration in impaction bone grafting, THE JOURNAL OF BONE AND JOINT SURGERY, Vol. 81-B, No. 1, January 1999).

Accordingly, a need may exist for an improved self-clearing rasp system capable of self-generating forces for pushing material against the rasp surface for providing an automatic milling apparatus capable of consistently providing superior morselized bone with similar particle-size distribution profile as planned.

Therefore, the main object of the present invention is to provide a self-clearing rasp system with self-generating forces for pushing the material against the rasp that may eliminate the need for skilled operator involvement.

It is another object of this invention to provide a self-clearing rasp system capable of consistently and repeatedly producing morselized bone with similar particle-size distribution profile within the constrained time limitation during a surgical procedure, regardless of the hardness and density of the bone material.

Moreover, it is another object of this invention to provide a self-clearing rasp system providing capabilities for predictably shifting the mean and broadening the standard deviation of the milled particle-size distribution profile during a given surgical procedure with the same rasp system.

Further, another object of this invention is to provide examples of automatic milling apparatuses utilizing said self-clearing rasp systems for automatic milling bone material at low temperature, repeatedly and efficiently producing bone particles with similar particle-size distribution profile as planned.

SUMMARY OF THE INVENTION

In some embodiment, self-clearing rasp systems that may have capability of producing morselized bone with predetermined particle-size distribution for automatic milling apparatus disclosed. The rasp systems comprises a rasp for cutting material and a trimming member for trimming cut material within predetermined particle sizes and having a push surface to direct the material toward the rasp for milling, disclosed. The rasp having flat or curved surface may comprise raised cutting teeth having angled faces with aperture sizes equal or larger than the angled faces of the cutting teeth disposed adjacent to the front or back, or both faces and disposed for sieving and removing particles from the surface of the rasp, disclosed. The disclosed trimming member may comprise an angled push surface, leading trimming edge, and trimming teeth with trimming edges that may approximately correspond to the contour of the said rasp-cutting teeth face.

In addition, embodiments of two radial self-clearing rasp systems with self-generating centrifugal forces for pushing material against the rasp surface for automatic milling apparatus disclosed. The said radial rasp systems may comprise radial rasp and radial trimming member comprising radial channels and push surface, moving and reciprocating clockwise and counterclockwise or ramping revolving speed up and down respect to each other for automatic milling, disclosed. One of the disclosed rasp systems may provide capabilities for predictably shifting the mean particle-size and adjusting the standard deviation of the particle-seize distribution profile, which may provide as a universal rasp system.

Furthermore, as examples, embodiments of two automatic milling apparatuses for automatic milling bone material utilizing said radial self-clearing rasp systems disclosed.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

FIG. 17A is a perspective view of an embodiment of radial rasp system 1000;

FIG. 17B is a perspective view of an embodiment of a cross feeder 804;

FIG. 17C is a perspective view of inside of the spindle 800;

FIG. 17D is a perspective view of an embodiment of rasp 900;

DETAILED DESCRIPTION

Various embodiments of the invention are now described with reference to the Figures, where like reference numbers indicate identical or functionally similar elements. The embodiments of the present invention, as generally described, and illustrated in the Figures herein could be arranged and designed in a wide variety of different configurations. Thus, the following more detailed description of several exemplary embodiments of the present invention, as represented in the Figures, is not intended to limit the scope of the invention, as claimed, but is merely representative of the embodiments of the invention.

The word "exemplary" is used exclusively herein to mean "serving as an example, instance, or illustration." Any embodiment described herein as "exemplary" is not necessarily to be construed as preferred or advantageous over other embodiments.

As used herein, the terms "an embodiment," "embodiment," "embodiments," "the embodiment," "the embodiments," "one or more embodiments," "some embodiments," "certain embodiments," "one embodiment," "another embodiment" and the like mean "one or more (but not necessarily all) embodiments of the disclosed invention(s)," unless expressly specified otherwise.

The phrase "based on" does not mean "based only on," unless expressly specified otherwise. In other words, the phrase "based on" describes both "based only on" and "based at least on."

Figure 1:
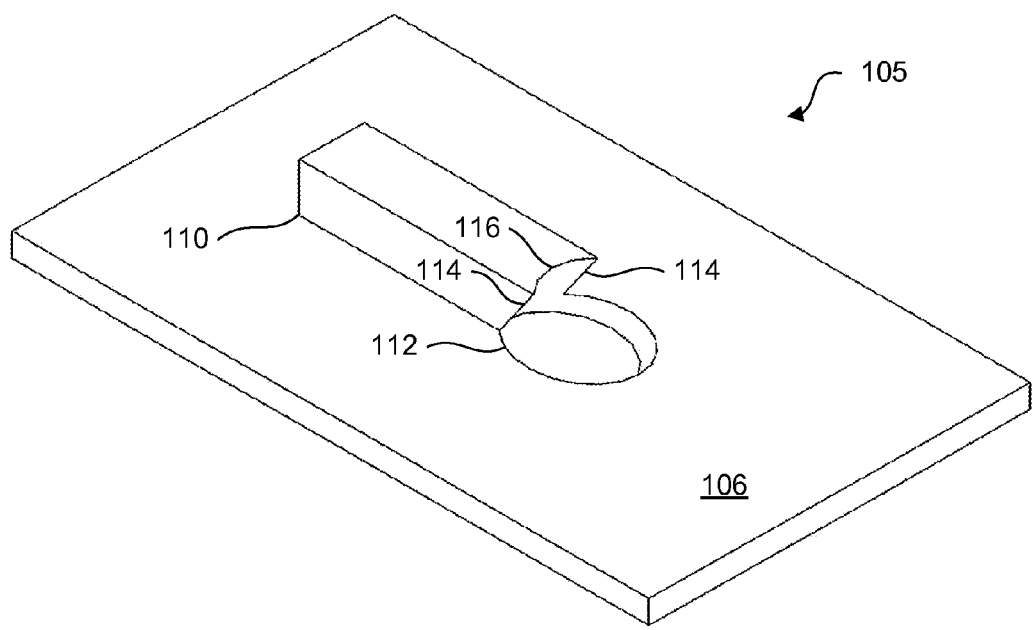
FIG. 1 is a perspective cut away of an embodiment of a rasp for milling material.
Figure 2:
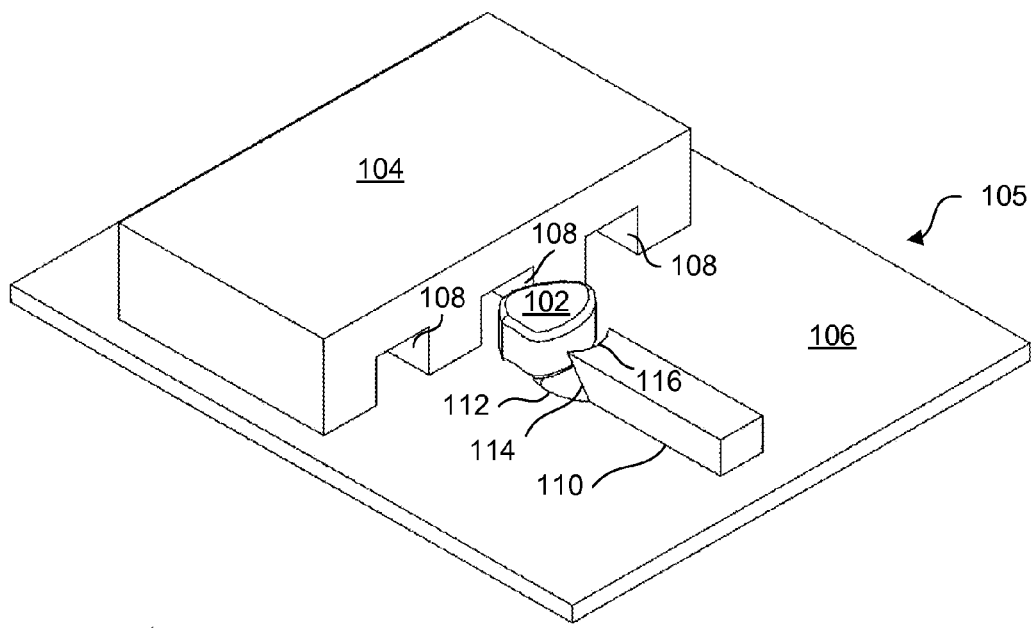
FIG. 2 is a perspective cut away of an embodiment of a rasp and trimming member for milling material.

FIG. 1 is a perspective cut away of an embodiment of a rasp 105 for milling material 102. FIG. 2 is a perspective cut away of an embodiment of a rasp 105 and trimming member 104 for milling material 102. The rasp 105 may include a base surface 106. The trimming member 104 may include ribs 108. The base surface 106 includes a cutting tooth 110 and an aperture 112. The cutting tooth 110 may protrude from the base surface 106. The cutting tooth 110 may include an inclined face 114. The inclined face 114 of the cutting tooth 110 may terminate in a cutting edge 116.

The rasp 105 and the trimming member 104 may move relative to each other. For example, the rasp 105 may move with respect to the trimming member 104, the trimming member 104 may move with respect to the rasp 105, and/or the rasp 105 and the trimming member 104 may move with respect to each other. The rasp 105 and the trimming member 104 may move radially, longitudinally, or in any other direction that may allow the rasp 105 and the trimming member 104 to interface to mill material 102 placed on the base surface 106.

The rasp 105 and the trimming member 104 may interface to mill material 102 placed on the base surface 106. For example, the cutting tooth 110 may pass near a rib 108 when the rasp 105 and the trimming member 104 move with respect to each other. In the present embodiment, the cutting tooth 110 may pass near two ribs 108 when the base surface 106 and the trimming member 104 move with respect to each other.

The aperture 112 may be arcuately aligned with the inclined face 114 of the cutting tooth 110. For the purpose of this disclosure, arcuately aligned may include aligning a portion of the inclined face 114 with a portion of the aperture 112.

For example, the aperture 112 and the inclined face 114 may be formed by drilling into the rasp 105. A drill may enter the rasp 105 at an angle that is not perpendicular to the base surface 106, such that an axis of the inclined face 114 and an axis of the aperture 112 may be at an angle from the base surface 106 of less than approximately ninety degrees. This may facilitate the sieving action of the milled material 102 as will be explained further below.

The cutting tooth 110 may engage a piece of the material 102 to be milled. For example, the cutting tooth 110 may push the material 102 toward the trimming member 104. The material 102 may abut the trimming member 104. The cutting tooth 110 may remove a portion of the material 102 when the material 102 abuts the trimming member 104 and the cutting tooth 110. In this manner, material 102 may be cut rather than crushed, which may heat and potentially damage the material 102.

The aperture 112 and the inclined face 114 may cooperate to direct the removed portion of the material 102 through the aperture 112 below the base surface 106. For example, as the cutting tooth 110 removes a portion of the material 102, the removed portion of the material 102 may abut the inclined face 114 and a portion of the aperture 112 such that the removed portion of the material 102 may be pushed below the base surface 106. In this manner, the base surface 106 and the aperture 112 act much like a sieve to allow only material of a desired size or smaller to pass through the base surface 106. In other embodiments, the base surface 106 may not be located below the material 102 such that removed portions of the material 102 may pass through the apertures 112 with the aid of gravity, but rather may be located above the material 102 such that removed portions of the material 102 may pass through the apertures 112 with the aid of another force, such as a force created by the angle of the inclined face 114 and/or other force.

The size of the aperture 112 and/or the angle of the inclined face 114 may be selected to achieve a predetermined particle size distribution profile. The cutting tooth 110 may remove portions of the material 102 that are approximately the size of the aperture 112, smaller than the size of the aperture 112, and/or larger than the size of the aperture 112. When a removed portion of the material 102 is larger than the size of the aperture 112, the cutting tooth 110 may push the removed portion of the material 102 into the trimming member 104 and remove another portion of the material 102. This process may be repeated until all of the material 102 to be milled has been directed through the aperture 112.

Particle size distribution profiles may include the varying sizes of the milled material 102. The particle size distribution profile may represent a bell shaped curve of the various particle sizes. In some embodiments, after milling the material 102, the particle size distribution profile may include a small range of particle sizes. A particle size distribution profile with a small range of particle sizes may be advantageous in applications requiring specific profiles.

The rasp 105 may include apertures 112 of varying diameters and/or cutting teeth 110 of varying sizes. For example, one aperture 112 may have a first predetermined diameter and/or cutting tooth 110 size, a second aperture 112 may have a second predetermined diameter and/or cutting tooth 110 size, and a third aperture 112 may have a third predetermined diameter and/or cutting tooth 110 size. Varying the diameters, or sizes, of the apertures 112 and/or cutting teeth 110 may facilitate achieving desired particle size distribution profiles.

Figure 3:
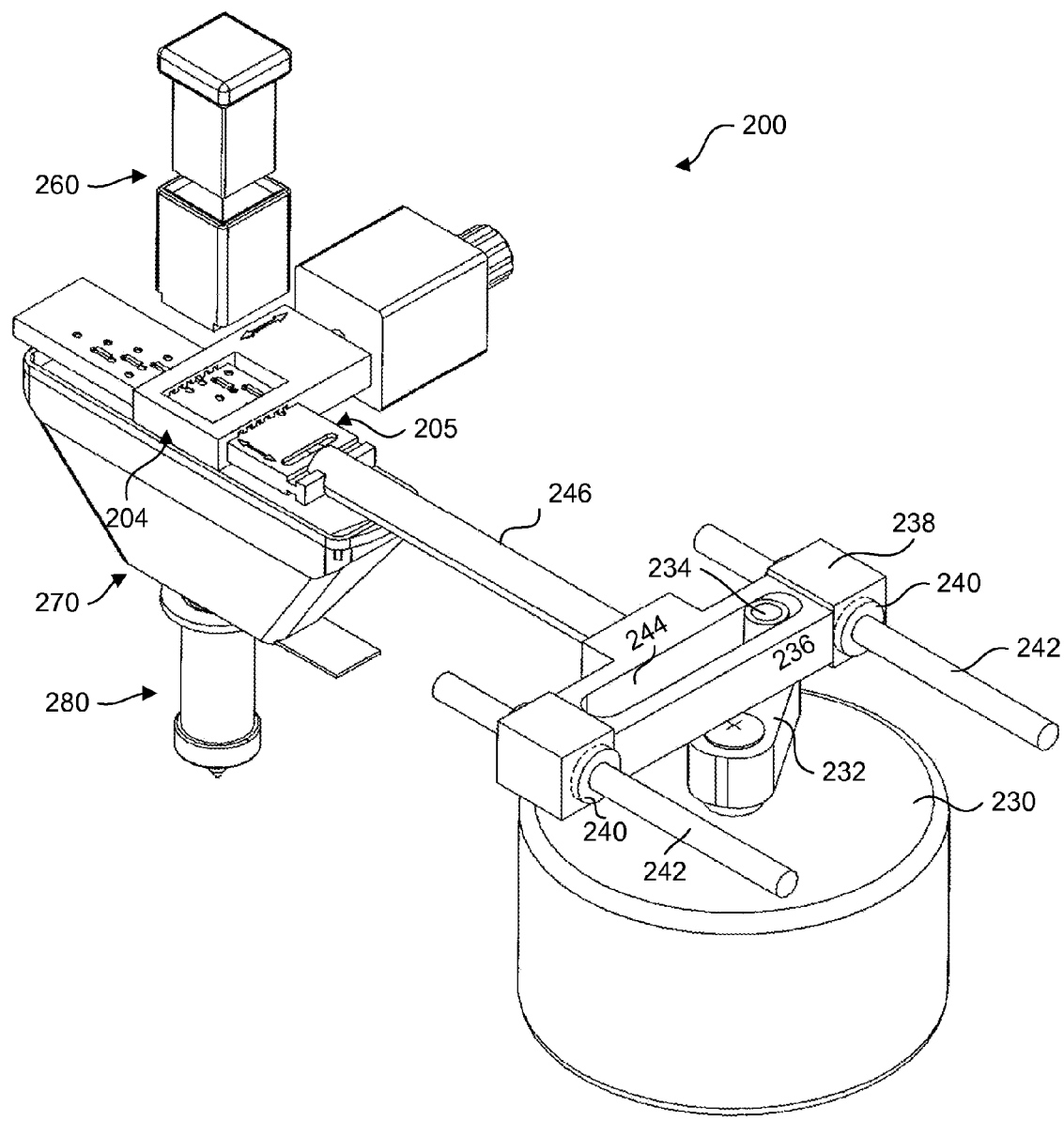
FIG. 3 is a perspective view of a longitudinal embodiment of an apparatus for milling material.

FIG. 3 is a perspective view of a longitudinal embodiment of an apparatus 200 for milling material 102. The apparatus 200 may include a rasp 205 and a trimming member 204.

The apparatus 200 may include a hopper assembly 260, a collector assembly 270, and/or a dispenser 280. These elements will be discussed in more detail in connection with FIGS. 5-7.

The present embodiment is a longitudinal embodiment of an apparatus 200 for milling material 102, because the rasp 205 and the trimming member 204 may move longitudinally relative to each other. The rasp 205 may be moved relative to the trimming member 204 by a driving mechanism. A driving mechanism may include any mechanism that may move the rasp 205 and/or the trimming member 204 with respect to each other. For example, a driving mechanism may include a user that may move the rasp 205 and/or the trimming member 204 with respect to each other. In another example, a driving mechanism may include a motor that may move the rasp 205 and/or the trimming member 204 with respect to each other. In the present embodiment, the driving mechanism may include a rotary motor 230 and a linear motor 231.

The rotary motor 230 may rotate a cam 232. The cam 232 may include a pin 234, which may be connected to a bearing 236. The cam 232 may move a sliding mechanism 238. The sliding mechanism 238 may include linear bearings 240. The linear bearings 240 may slide on two bars 242. The pin 234 of the cam 232 with its bearing 236 may be contained within a slot 244. The pin 234 may drive the sliding mechanism 238 such that the sliding mechanism 238 generates reciprocating linear motion. The sliding mechanism 238 may be connected to a member 246. The member 246 may translate the force from the sliding mechanism 238 to the rasp 205, such that the rasp 205 moves reciprocally in a longitudinal direction (as shown by arrow A) relative to the trimming member 204.

The linear motor 231 may move both the rasp 205 and the trimming member 204 in a lateral direction (as shown by arrow B). This motion will be discussed in more detail in connection with FIG. 5.

Figure 4:
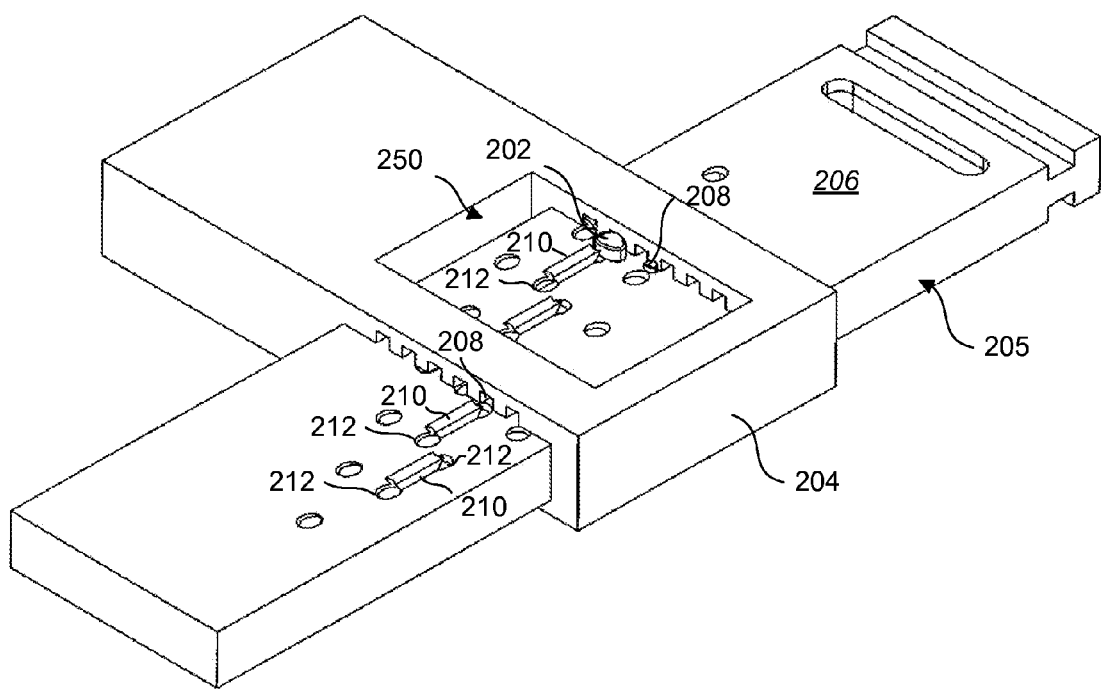
FIG. 4 is a perspective view of the rasp and trimming member of the longitudinal embodiment of the apparatus for milling material shown in FIG. 3.

FIG. 4 is a perspective view of the rasp 205 and trimming member 204 of the longitudinal embodiment of the apparatus 200 for milling material 102 shown in FIG. 3. The base surface 206 may include multiple cutting teeth 210. The cutting teeth 210, in the present embodiment, may be laterally offset from each other. For example, the cutting teeth 210 may be offset from each other in a direction perpendicular to the direction of the relative motion between the rasp 205 and the trimming member 204. The cutting teeth 210 may be longitudinally offset from each other. For example, the cutting teeth 210 may be offset from each other in the direction of the relative motion between the rasp 205 and the trimming member 204.

In the present embodiment, the cutting teeth 210 are both laterally and longitudinally offset from each other, such that no cutting tooth 210 is aligned longitudinally or laterally with another tooth 210. The trimming member 204 may include multiple ribs 208 that may interface with the various cutting teeth 210. The trimming member 204 may include an opening 250. The opening 250 may generally enclose the material 102 to be milled. In the present embodiment, the opening 250 may cut through a portion of the trimming member 204 that includes the ribs 208 such that one portion of the ribs 208 is separated from another portion of the ribs 208.

The base surface 206 may include multiple apertures 212. In the present embodiment, two apertures 212 may be disposed adjacent a cutting tooth 210. For example, the one aperture 212 may be positioned near one inclined face 214 of a cutting tooth 210 and another aperture 212 may be positioned near the other inclined face 214 of the cutting tooth 210. The base surface 206 may include other apertures 212 that may not necessarily be disposed adjacent a cutting tooth 210.

The size of the various apertures 212 and/or the angle of the inclined faces 214 may be selected to achieve a pre-determined particle size distribution profile. For example, some cutting teeth 210 may be different sizes than other cutting teeth 210 and/or some apertures 212 may be different sizes than other apertures 212. In another example, some cutting teeth 210 may include inclined faces 214 of different shapes than other inclined faces 214 and/or some apertures 212 may be of different shapes than other apertures 212.

The cutting tooth 210 may remove portions of the material 102. The removed portions of the material 102 may be of varying sizes. For example, portions of the material 102 may be removed that are approximately the size of the aperture 212, smaller than the size of the aperture 212, and/or larger than the size of the aperture 212. When a removed portion of the material 102 is larger than the size of the aperture 212, a cutting tooth 210, i.e. the same or a different cutting tooth 210, may push the removed portion of the material 102 into the trimming member 204 and remove another portion of the material 102. This process may be repeated until all of the material 102 to be milled has been directed through the aperture 212. Thus, the material 102 may be cut to generally match a predetermined varied particle size distribution profile.

The present embodiment is a longitudinal embodiment of an apparatus 200 for milling material 102, because the rasp 205 and the trimming member 204 may move longitudinally relative to each other. For example, the rasp 205 may be moved using the rotary motor 230 shown in the previous embodiment (shown in FIG. 3).

The rasp 205 may move reciprocally in a longitudinal direction relative to the trimming member 204. In embodiments where the base surface 206 may include a cutting tooth 210 with more than one cutting edge 216 and inclined face 214, this reciprocal motion may allow the cutting tooth 210 to remove portions of the material 102 to be milled on both the forward and the backward stroke of the rasp 205. For example, if the rasp 205 moves reciprocally, a cutting tooth 210 may remove portions of the material 102 to be milled as the rasp 205 and/or the trimming member 204 moves away from a driving mechanism (i.e. the forward stroke) and the cutting tooth 210 may remove portions of the material 102 to be milled as the rasp 205 and/or the trimming member 204 moves toward the driving mechanism (i.e. the backward stroke).

Figure 5:
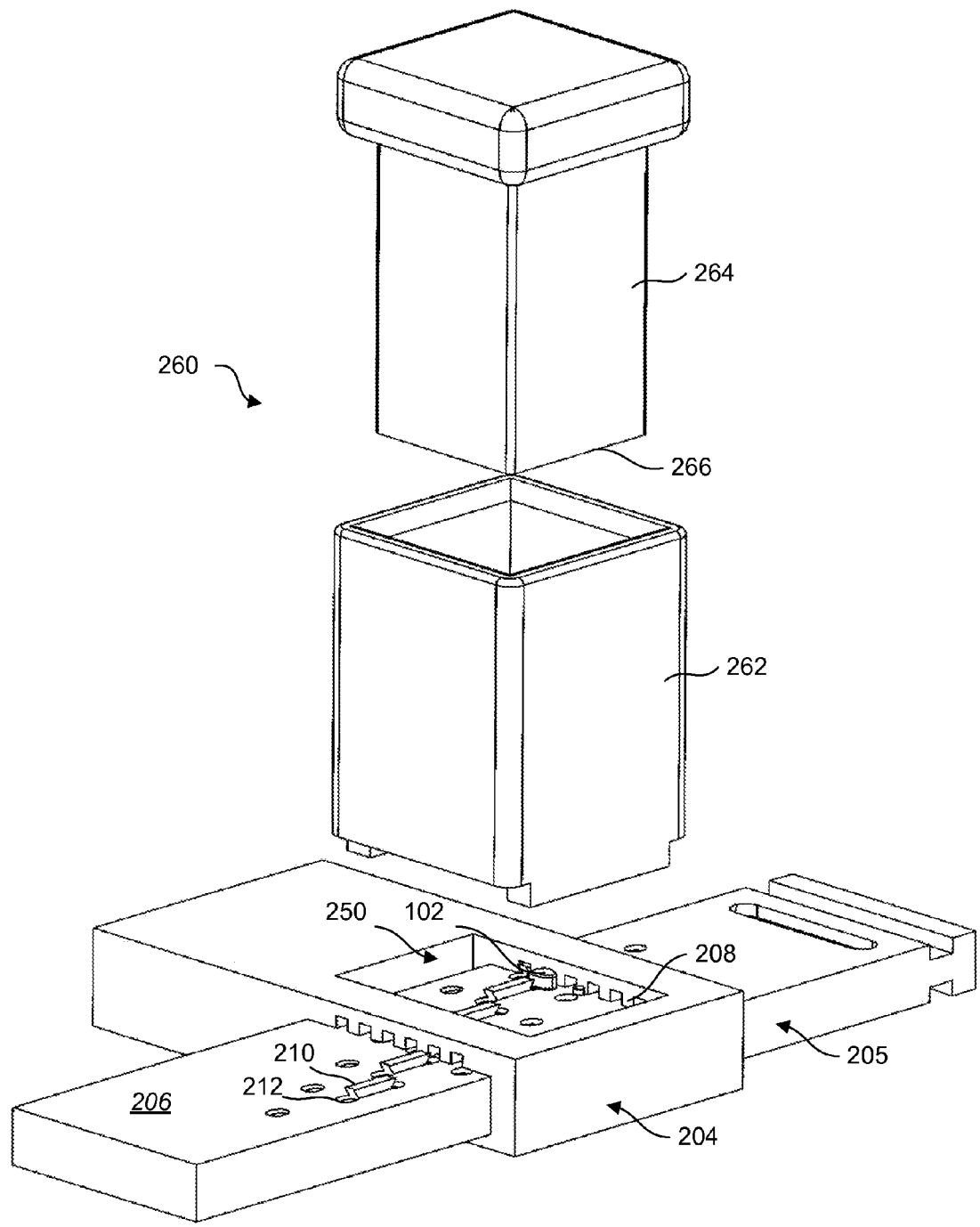
FIG. 5 is a perspective partially exploded view of a hopper assembly used in conjunction with the longitudinal embodiment of an apparatus for milling material shown in FIG. 3.

FIG. 5 is a perspective partially exploded view of a hopper assembly 260 used in conjunction with the longitudinal embodiment of an apparatus 200 for milling material 102 shown in FIG. 3. The hopper assembly 260 may include a stationary chute 262 and a push rod 264. The base surface 206 of the rasp 205 may include multiple cutting teeth 210 and apertures 212, as in the previous embodiments.

The trimming member 204 may include multiple ribs 208. The trimming member 204 may include an opening 250. The opening 250 may generally enclose the material 102 to be milled. The opening 250 may be disposed to receive the stationary chute 262 and/or push rod 264. The opening 250 may be disposed to receive the stationary chute 262 such that the stationary chute 262 may be partially inserted into the opening 250. The stationary chute 262 may also generally enclose the material 102 to be milled. The stationary chute 262 may allow the apparatus 200 to mill more material 102 by providing a temporary container for material 102 to be milled as the apparatus mills the material 102 that is within the opening 250 of the trimming member 204. For example, the stationary chute 262 may act like a hopper or the like.

The push rod 264 may be used to apply pressure to the material 102 to be milled such that it may be pressed against the base surface 206. The push rod 264 may include a push surface 266. The push surface 266 may interface with the material 102 to be milled. The push rod 264 may prevent material 102 from merely being chipped by a cutting tooth 210 by generally restraining the vertical motion of the material. For example, a piece of material 102 may be pressed against the base surface 206 by both the push rod 264 and the force of gravity such that as the cutting tooth 210 pushes the piece of material 102 against the trimming member 204, the cutting tooth 210 may remove a portion of the material 102.

During the cutting process, the material 102 to be milled and the stationary chute 262 may remain stationary. The rasp 205 may move in the longitudinal direction (as shown by arrow A) allowing the cutting teeth 210 to remove portions of the material 102. The rasp 205 and trimming member 204 may also move in the lateral direction (as shown by arrow B) such that a cutting tooth 210 that has previously cut a portion of the material 102 and/or another cutting tooth 210 may, by moving in the lateral direction with respect to the stationary material 102, cut a different portion of the material 102. This may prevent the material 102 to be milled from simply being recut by the various cutting teeth 210 with which it may come in contact.

For example, if the material 102 stays in the same position within the opening 250, i.e. the material 102 does not move in either the longitudinal or the lateral direction, a cutting tooth 210 may cut a portion of the material 102 on the first stroke of the rasp 205 leaving a groove in the material 102. On the second stroke, the cutting tooth 210 may pass through the cut groove and may remove a minimal amount of material 102 on the second and subsequent strokes. In the present embodiment, the trimming member 204 and rasp 205 may move approximately the width of one cutting tooth 210 on each stroke in the lateral direction with respect to the stationary chute 262 and the material 102 to be milled.

Figure 6:
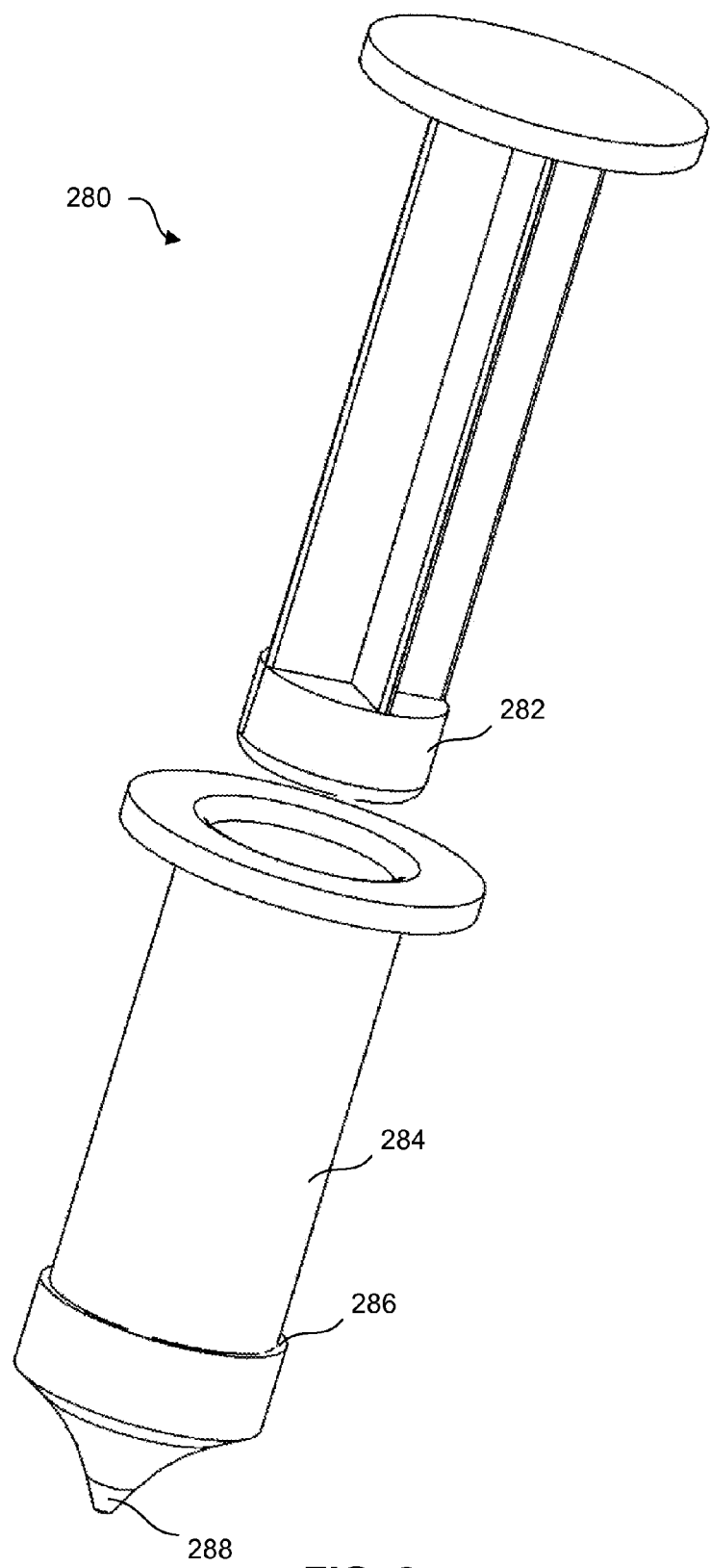
FIG. 6 is a perspective exploded view of a dispenser.

FIG. 6 is a perspective exploded view of an embodiment of a dispenser 280. The dispenser 280 may include a plunger 282. The dispenser 280 may include a boot 284. The boot 284 may include a tip 286. The tip 286 may include a hole 288 that may enlarge to facilitate dispensing of the milled material 102. For example, the dispenser 280 may contain some of the milled material 102. The plunger 282 may apply pressure to the milled material 102, which in turn may apply pressure to the tip 286 of the dispenser. As the plunger 282 applies pressure to the milled material 102, the milled material 102 may enlarge the hole 288 in the tip 286 of the dispenser 280 to allow the milled material 102 to pass therethrough.

The dispenser 280 may be used to combine the milled material 102 with other ingredients to make a bone paste. When a larger amount of bone paste is needed for larger segmental replacements in a surgical procedure a composite mixture may be used. For example, a composite mixture of calcium phosphate and collagen mixed with bone marrow and the milled material 102 may be used to fuse lumbar vertebrae. The dispenser 280 may also be used to dispense the bone paste.

Figure 7:
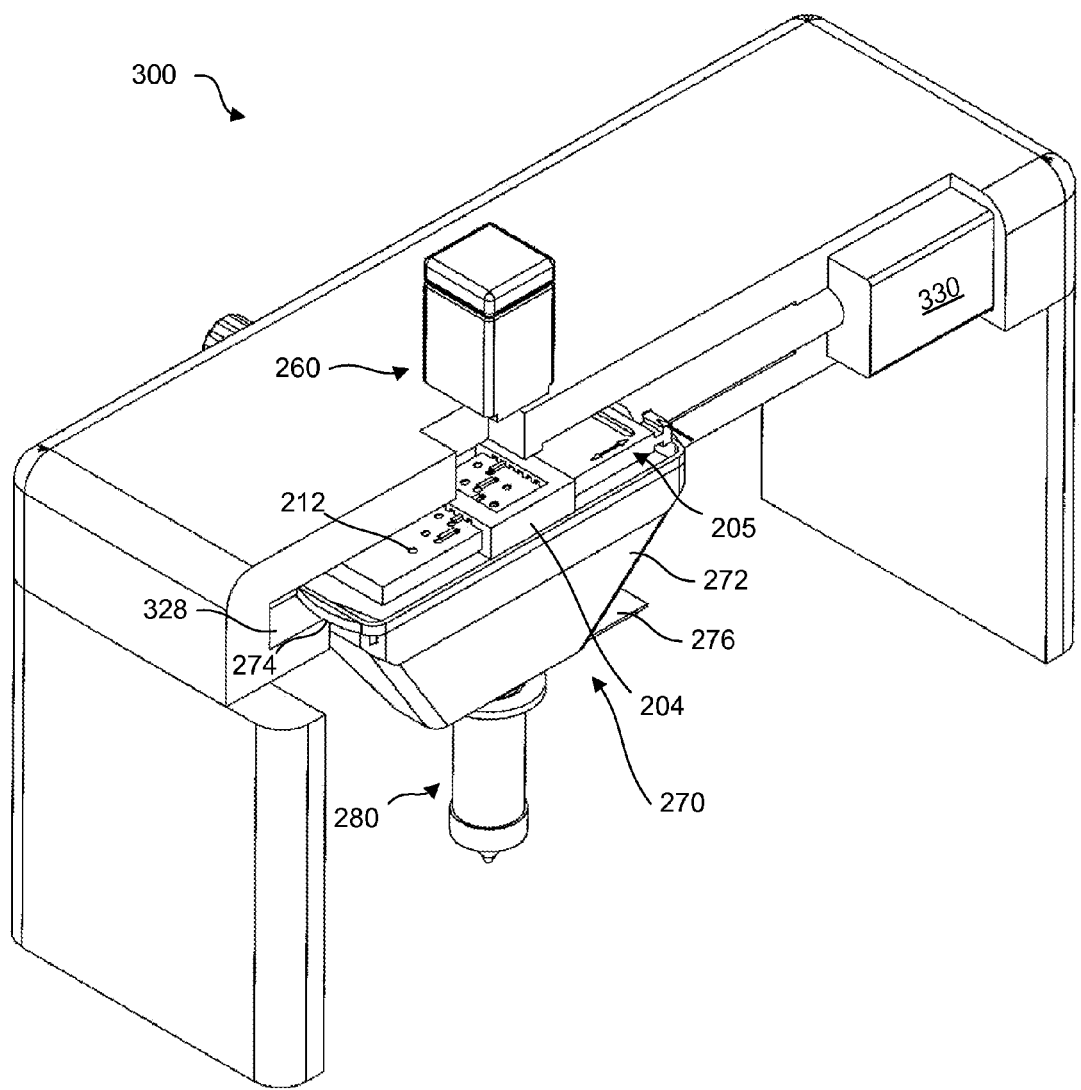
FIG. 7 is a perspective partially exploded sectional view of another longitudinal embodiment of an apparatus for milling material including a collector assembly for receiving the milled material.

FIG. 7 is a perspective partially exploded sectional view of another longitudinal embodiment of an apparatus 300 for milling material 102 including a collector assembly 270 for receiving the milled material 102. The apparatus 300 may include a linear motor 330 rather than the rotary motor 230 used in the previous embodiment (shown in FIG. 3). The apparatus 300 may include a hopper assembly 260.

The collector assembly 270 may include a container 272. The container 272 may include side lips 374. The side lips 374 of the container 272 may rest on a frame 328. The container 272 may be aligned with the rasp 205 and the trimming member 204 such that when the apparatus 200 is in use, the container 272 may receive the portions of the material 102 to be milled that pass through the apertures 212 in the base surface (not shown). In the present embodiment, the collector assembly 270 may be connected to a dispenser 280. The dispenser 280 may fill with material 102 that enters the container 272.

The container 272 may also include a gate 276. The gate 276 may be used to prevent the milled material 102 from entering the dispenser 280. For example, the gate 276 may be used to prevent any additional material 102 from entering the dispenser 280 after the dispenser has been filled. In another example, the gate 276 may be used to allow the container 272 to fill with material 102 to a certain point before removing the gate 276.

Figure 8:
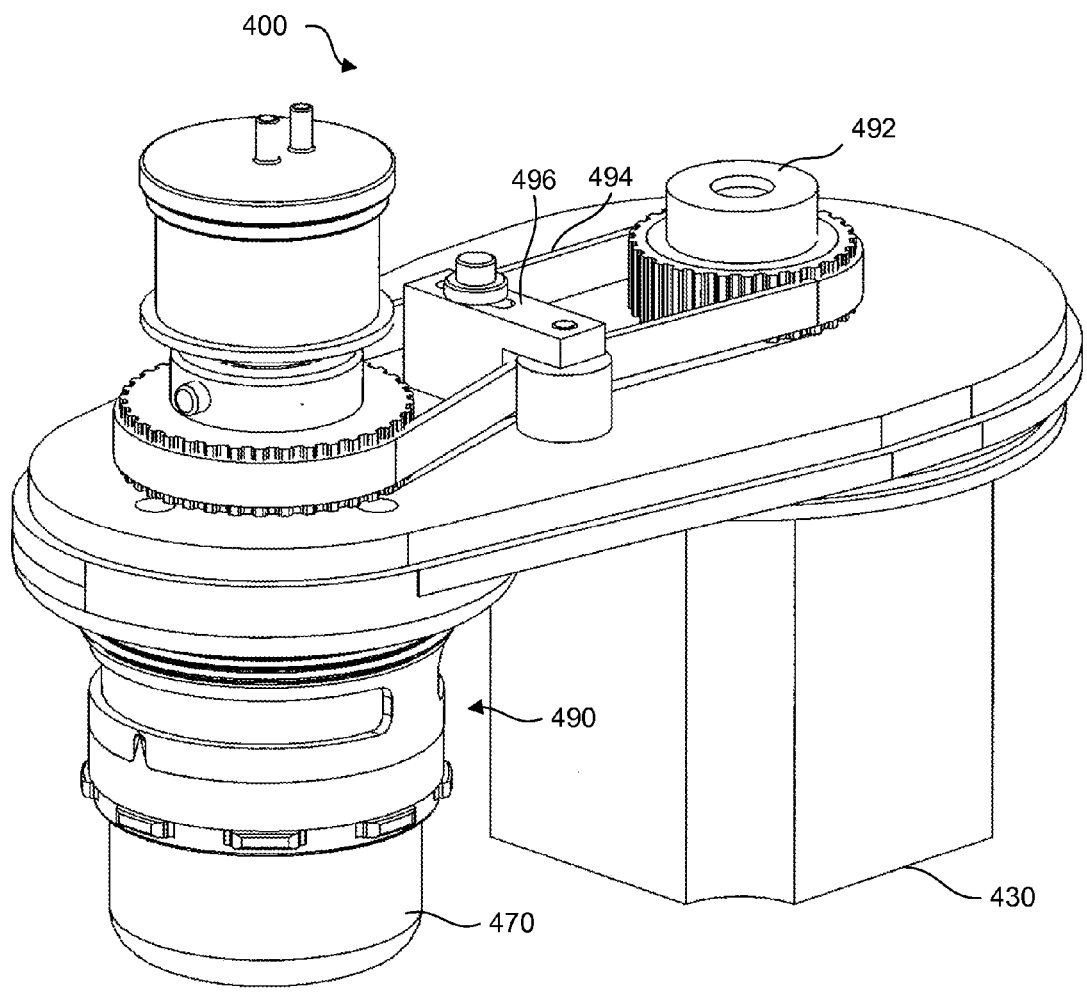
FIG. 8 is a perspective view of a partially assembled radial embodiment of an apparatus for milling material.

FIG. 8 is a perspective view of a partially assembled radial embodiment of an apparatus 400 for milling material 102. The apparatus 400 may include a motor 430 and a milling portion 490. The milling portion 490 may include a base surface (not shown), a trimming member (not shown), and a liner (not shown). The milling portion 490 may be connected to a collector assembly 470. The milling portion 490 may include a spindle (not shown). The motor 430 may drive a pulley 492. The pulley 492 may be connected to a belt 494 that may rotate the spindle. A belt tensioner 496 may be connected to the apparatus 400. The belt tensioner 496 may be used to maintain a desired tension in the belt 494.

Figure 9:
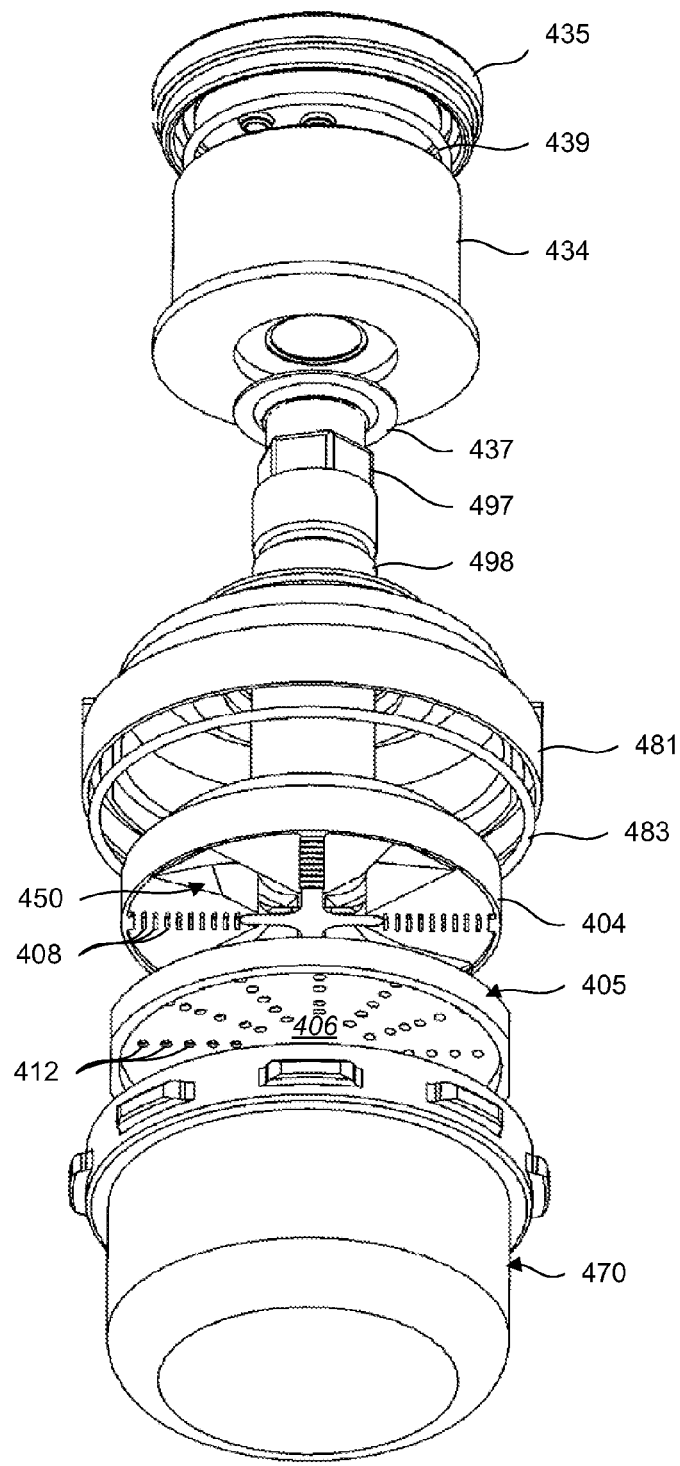
FIG. 9 is an exploded perspective view of another radial embodiment of an apparatus for milling material illustrating a collector assembly.

FIG. 9 is an exploded perspective view of another radial embodiment of an apparatus 400 for milling material 102 illustrating a collector assembly 470. The apparatus 400 may include a cover 435, a first sealing member 439 (for example, an O-ring), a funnel 434, a seal 437, a liner 481, a second sealing member 483, a coupling 497, and a spindle 498. These elements may be used to create an inner volume that is sealed, which may facilitate milling the material 102 in an airtight, sealed environment. For example, the liner 481, the second sealing member 483, and the collector assembly 470 may be connected to facilitate sealing this inner volume.

The trimming member 404 may include ramped openings 450 (similar to the openings 250 shown in conjunction with FIG. 3) between the ribs 408 that may allow the material 102 to interface with the rasp 405. The collector assembly 470 may be aligned with the rasp 405 and the trimming member 404 such that when the apparatus 400 is in use, the collector assembly 470 may receive the portions of the milled material 102 that pass through the apertures 412 in the base surface 406.

Figure 10:
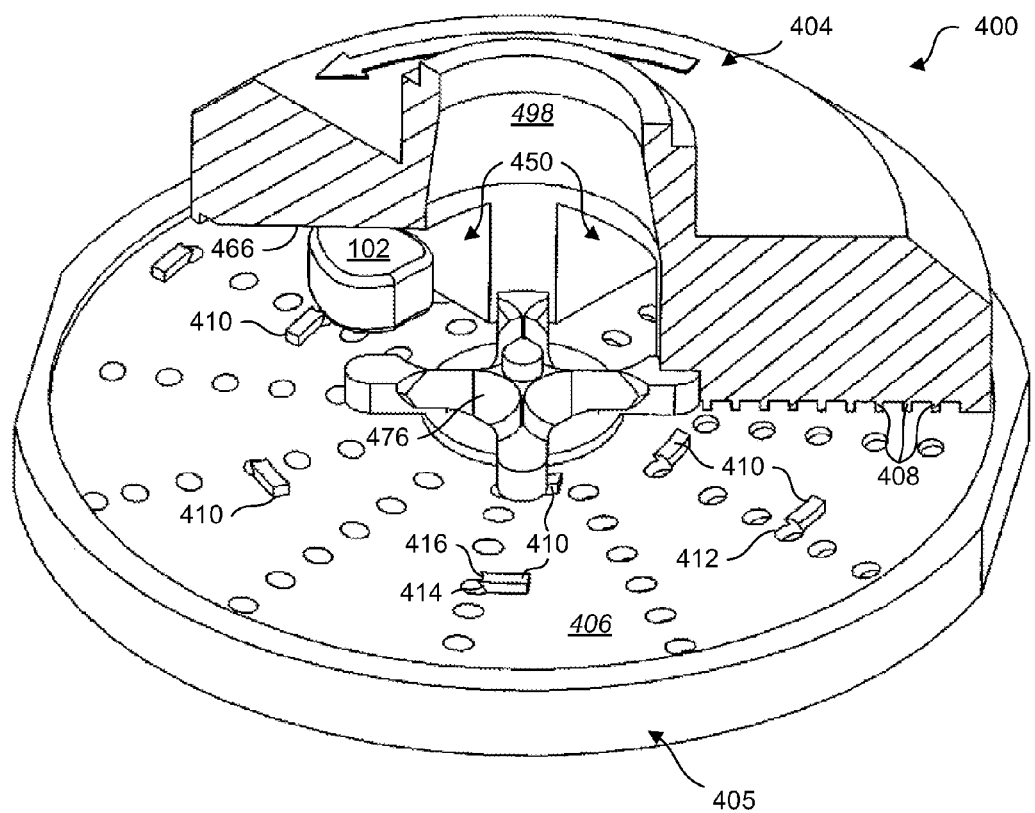
FIG. 10 is a perspective sectional view of the radial embodiment of the apparatus for milling material shown in FIG. 8.
Figure 11:
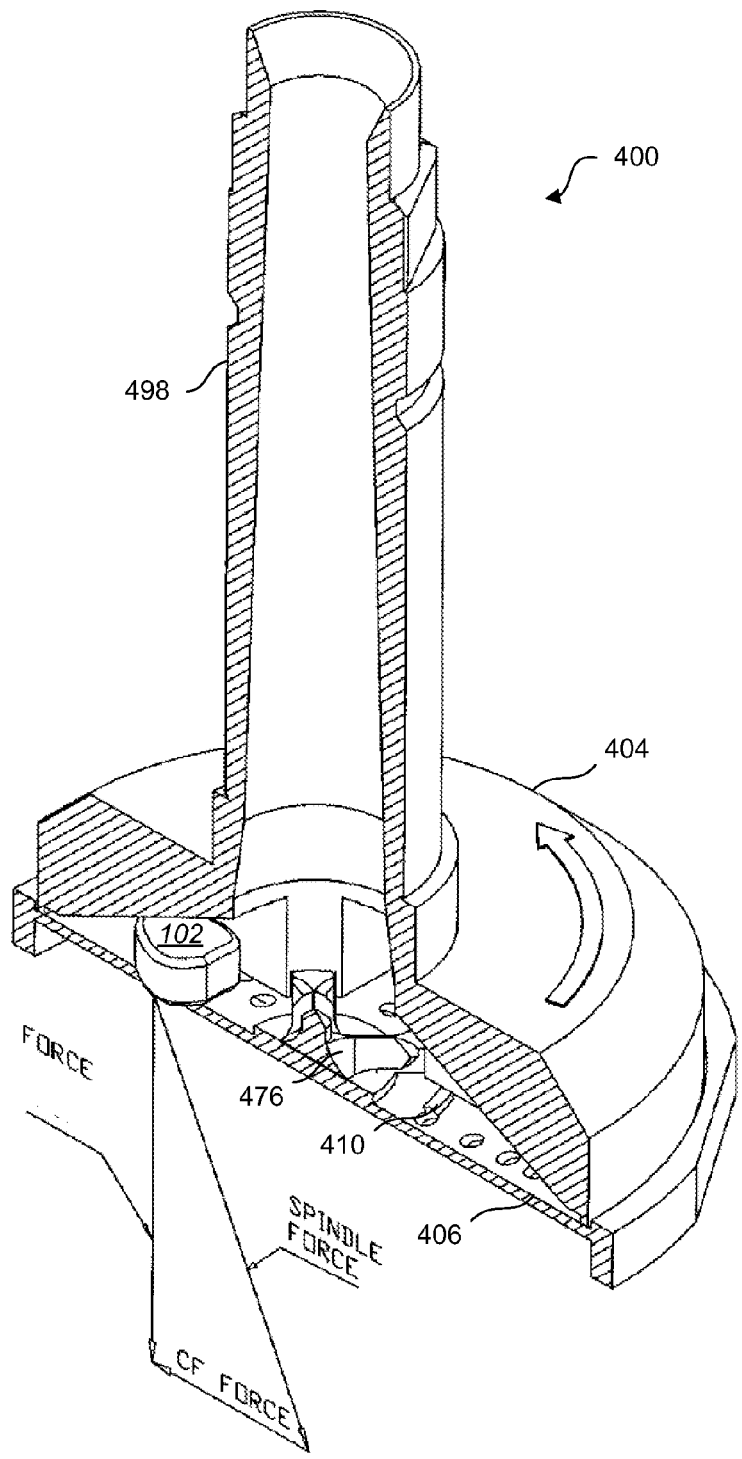
FIG. 11 is a perspective sectional view of the radial embodiment of the apparatus for milling material shown in FIG. 8.
Figure 12:
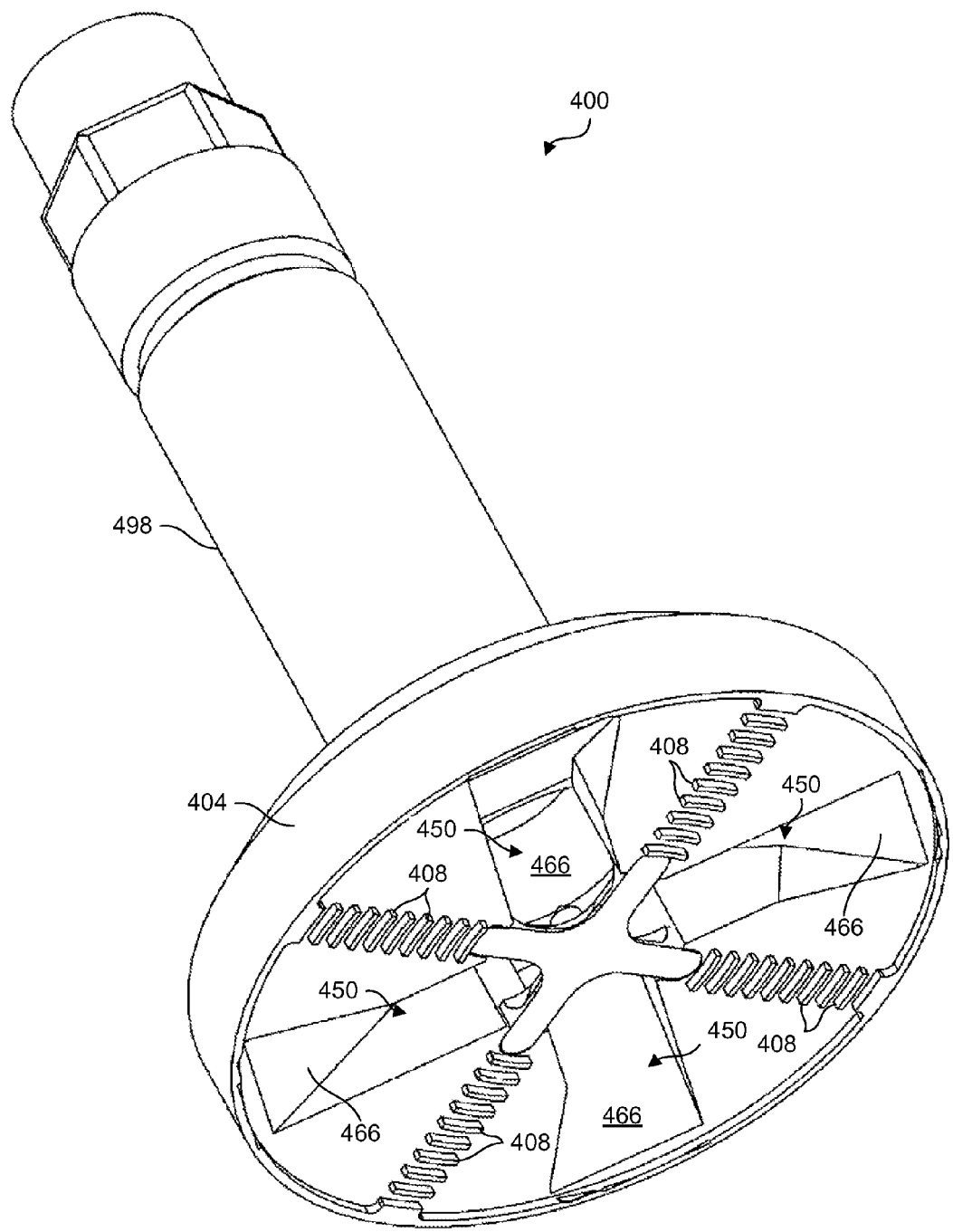
FIG. 12 is a perspective view of a spindle and trimming member of the radial embodiment of the apparatus for milling material shown in FIG. 8.

FIGS. 10, 11, and 12 are perspective sectional views of the radial embodiment of an apparatus 400 for milling material 102 shown in FIG. 8. The apparatus 400 may include a rasp 405 and a trimming member 404.

As shown in FIG. 10, the base surface 406, like the embodiment of FIG. 3, may include multiple cutting teeth 410. The cutting teeth 410, in the present embodiment, may be radially offset from each other. For example, the cutting teeth 410 may be offset from each other along a radius of the base surface 406. The cutting teeth 410 may be circumferentially offset from each other. For example, the cutting teeth 410 may be offset from each other along a circumference of the base surface 406.

In the present embodiment, some of the cutting teeth 410 are not radially offset from each other and some of the cutting teeth 410 are not circumferentially offset from each other. The trimming member 404 may include multiple ribs 408 that may interface with the various cutting teeth 410.

As shown in detail in FIG. 10, the trimming member 404 may include a ramped opening 450. The ramped openings 450 may include push surfaces 466. The ramped opening 450 and push surface 466 may cooperate to push the material 102 to be milled against the base surface 406 of the rasp 405. The ramped opening 450 may generally enclose the material 102 to be milled. In the present embodiment, the ramped opening 450 may cut through a central portion of the trimming member 404. The ramped openings 450 may include channels circumferentially between sets of ribs 408. The channels may allow the material 102 to abut the trimming member 404 and/or the push surface 466.

The base surface 406 in the present embodiment, like the base surface 206 in the embodiment of FIG. 3, may include multiple apertures 412. In the present embodiment, only one aperture 412 may be disposed adjacent a cutting tooth 410 because, in the present radial embodiment, the base surface 406 and the trimming member 404 generally may move reciprocally to facilitate disorienting and radially moving the material in the wedge channel. In other embodiments, more than one aperture 412 may be disposed adjacent each cutting tooth 410 (to further increase the milling efficiency). For example, in embodiments where the base surface 406 and the trimming member 404 move reciprocally, the cutting teeth 410 may include multiple inclined faces 414, cutting edges 416, and/or apertures 412. The base surface 406 may also include other apertures 412 that may not necessarily be disposed adjacent a cutting tooth 410.

The size of the various apertures 412 and/or cutting teeth 410 as well as the angle of the inclined faces 414 may be selected to achieve a pre-determined varied particle size distribution profile. For example, some cutting teeth 410 may be different sizes than other cutting teeth 410, some cutting teeth 410 may include inclined faces 414 of different shapes than other inclined faces 414, some apertures 412 may be different sizes than other apertures 412, and/or some apertures 412 may be of different shapes than other apertures 412. The ribs 408 may also have varied sizes.

The cutting tooth 410 may remove portions of the material 102. The removed portions of the material 102 may be of varying sizes. For example, portions of the material 102 may be removed that are approximately the size of the aperture 412, smaller than the size of the aperture 412, and/or larger than the size of the aperture 412. When a removed portion of the material 102 is larger than the size of the aperture 412, a cutting tooth 410, i.e. the same or a different cutting tooth 410, may push the removed portion of the material 102 into the trimming member 404 and remove another portion of the material 102. This process may be repeated until all of the material 102 to be milled has been directed through the aperture 412. Thus, the material 102 may be cut to generally match a predetermined varied particle size distribution profile.

The spindle 498 in the present embodiment is hollow. A hollow spindle 498 may work in conjunction with the funnel 434 to act as a hopper assembly 260 (shown in FIG. 5) to enclose the material 102 to be milled. The apparatus 400 may include a spider construct 476. The spider construct 476 may act as a cross-feeder. For example, as the material is fed through the hollow spindle 498, the spider construct 476 may direct the material 102 arriving at the opening 450 of the spindle 498 away from the center such that the material 102 may experience the radial centrifugal forces as the spindle 498 rotates.

The present embodiment is a radial embodiment of an apparatus 400 for milling material 102, because the base surface 406 and the trimming member 404 may move radially relative to each other. For example, the base surface 406 or the trimming member 404 may be rotated via a spindle 498. In another example, the base surface 406 or the trimming member 404 may be rotated via two separate spindles (not shown).

In the present embodiment, the base surface 406 does not move reciprocally (i.e. alternately clockwise and counterclockwise). In other embodiments, the base surface 406 may move reciprocally in a radial direction relative to the trimming member 404. In embodiments where the base surface 406 may include a cutting tooth 410 with more than one cutting edge 416 and inclined face 414, this reciprocal motion may allow the cutting tooth 410 to remove portions of the material 102 to be milled on both a clockwise and a counterclockwise rotation of the base surface 406. For example, if the base surface 406 moves reciprocally, a cutting tooth 410 may remove portions of the material 102 to be milled as the base surface 406 and/or the trimming member 404 rotates clockwise and the cutting tooth 410 may remove portions of the material 102 to be milled as the base surface 406 and/or the trimming member 404 rotates counterclockwise.

The apparatus 400 may include a push surface 466. The push surface 466 may be inclined with respect to the base surface 406 and may be used to direct the material 102 to be milled such that the material 102 may be pressed against the base surface 406. The push surface 466 may prevent material 102 from merely being chipped by a cutting tooth 410 by generally restraining the vertical motion of the material. However, as shown in detail in FIG. 10 and in contrast to the push rod 264 in the embodiment of FIG. 4, the push surface 466 may not apply pressure in response to a direct force on the push surface 466 toward the material 102 to be milled. Rather, the centrifugal forces that may be applied to the material 102 to be milled may direct the material 102 toward the push surface 466 such that the centrifugal forces push against the push surface 466. As shown in FIG. 11, the push surface 466 may generate a force to push the material 102 toward the base surface 406 such that as the cutting tooth 410 pushes the piece of material 102 against the trimming member 404 so that the cutting tooth 410 may remove a portion of the material 102.

Figure 13:
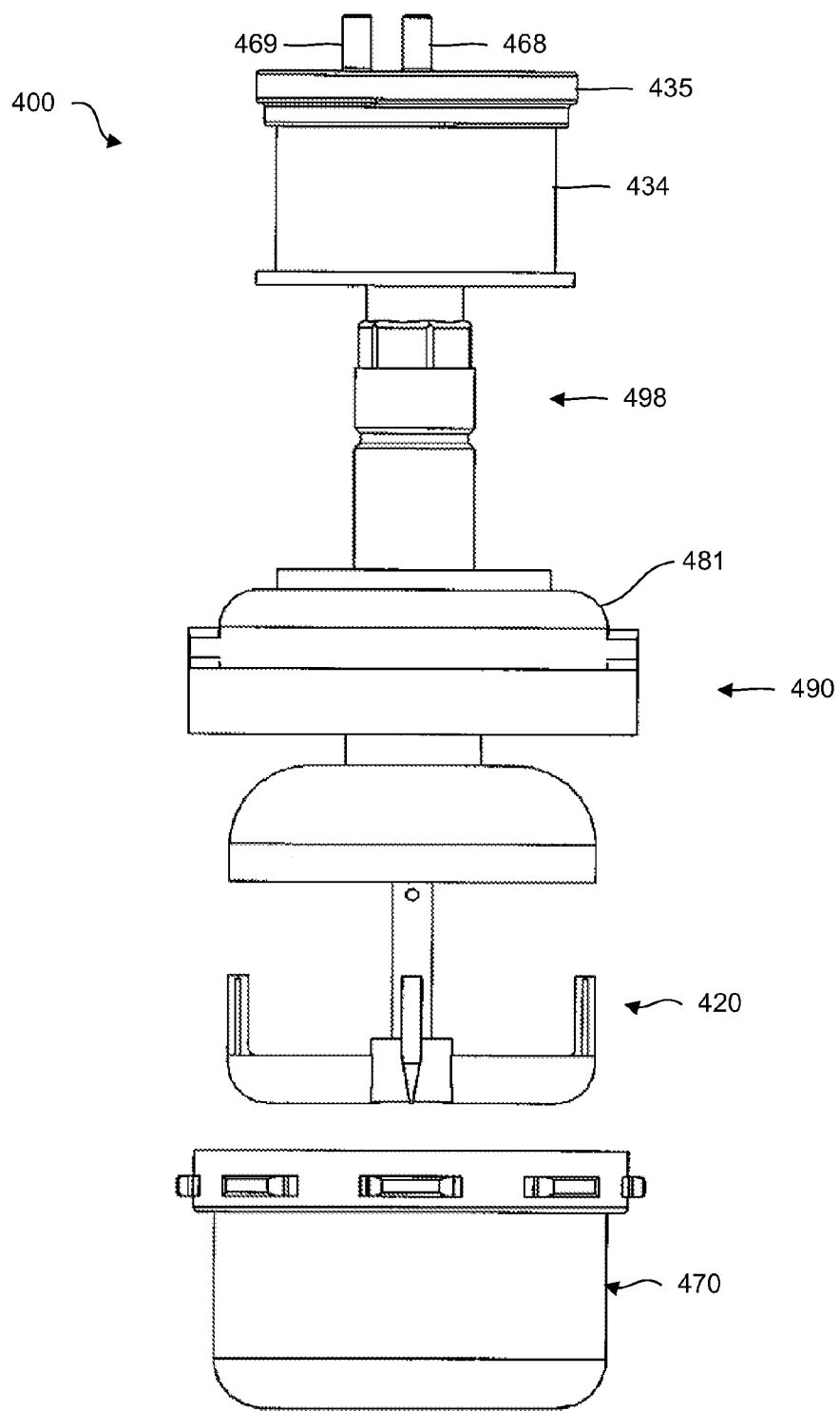
FIG. 13 is an exploded perspective view of another radial embodiment of an apparatus for milling material illustrating a mixing paddle, a collector assembly, and a milling portion.

FIG. 13 is a partially exploded front view of the radial embodiment of an apparatus 400 for milling material 102 illustrating a mixing paddle 420, a collector assembly 470, and a milling portion 490. The milling portion 490 may include a rasp (not shown), a trimming member (not shown), and a liner 481. The apparatus 400 may include a mixing paddle 420. The mixing paddle 420 may be connected to the spindle 498 such that as the spindle 498 rotates, the mixing paddle 420 may also rotate. In the present embodiment, the mixing paddle 420 may be separately connected to the spindle 498 after the rasp 405 (shown in FIG. 10) is removed. The collector assembly 470 may be removed to allow the rasp 405 and/or the trimming member 404 (shown in FIG. 10) to be removed from the spindle 498. The mixing paddle 420 may then be connected to the spindle 498 and the collector assembly 470 reconnected to the apparatus 400.

The apparatus 400 may include a funnel 434, a cover 435, and a spindle 498. These elements may be used to create an inner volume that is sealed, which may facilitate milling the material 102 in an airtight, sealed environment. The apparatus 400 may also include a fluid port 468 and a vacuum port 469. The fluid port 468 may be used to add fluids to the milled material 102. The fluids and milled material 102 may be mixed in the collector assembly 470 by the mixing paddle 420 to make a paste. Because the apparatus 400 may include a sealed inner volume, the vacuum port 469 may be used to create a vacuum within the sealed inner volume. Mixing under vacuum may facilitate replacing the air pockets in and around the milled material 102 with the added fluids. Moreover, mixing under vacuum may prevent aerating the paste during mixing.

In other embodiments, the mixing paddle 420 may be connected to the spindle 498 and located below the base surface (not shown). The mixing paddle 420 may be contained within the collector assembly 470. Thus, as the milled material 102 passes through the base surface (not shown) and is collected in the collector assembly 470, the mixing paddle 420 may mix the material 102. Other connections between the mixing paddle 420 and the spindle 498 are contemplated. For example, the mixing paddle 420 may be connected indirectly to the spindle 498 by a connection to the trimming member (not shown), the rasp (not shown), and/or other connections.

Various components of the disclosed apparatuses 200, 300, 400 may be disposable. For example, the rasps 205, 405, liner 481, and/or collection assembly 270, 470 may be removed and discarded after use. Other components of the disclosed apparatuses 200, 300, 400 may be autoclaved and reused.

The foregoing descriptions illustrate general principles that may be applied to mill material. The following is an example of a potential method for using these principles. Material 102 to be milled may be enclosed prior to being milled. For example, a hopper assembly 260 or a funnel 434 and hollow spindle 498 may enclose the material 102 to be milled.

A push surface, i.e. the push surface 266 of the push rod 264 (shown in FIG. 5) or the push surface 466 of the ramped openings 450 (shown in FIG. 10), may direct the material 102 to be milled toward the base surface 106 of the rasp 105. A cutting tooth 110 may engage a piece of the material 102 to be milled and may remove a piece of the material 102. The material 102 may be removed when the material 102 abuts the ribs 108 of the trimming member 104 and the cutting tooth 110. The milled material 102 may pass through the base surface 106 of the rasp 105 into a collector assembly 270, 470.

The milled material 102 may be mixed with other ingredients to form a paste. In some embodiments, the milled material 102 is mixed with other ingredients under a vacuum to prevent air pockets from entering the paste. The paste may be dispensed using a dispenser 280. Forming a paste with the freshly milled material 102 may provide an improved paste. For example, making a paste of a material 102 freshly milled from a bone may create a more effective paste for bone grafts.

The apparatuses 200, 300, 400 and methods disclosed may be particularly suitable for culling live bone chips, cutting the chips into a desired particle size distribution profile, making a paste of the cut chips, and/or applying the paste for use with a bone graft. The methods and apparatuses 200, 300, 400 may also be used in other applications where a desired particle size distribution profile may be desired.

Figure 14A:
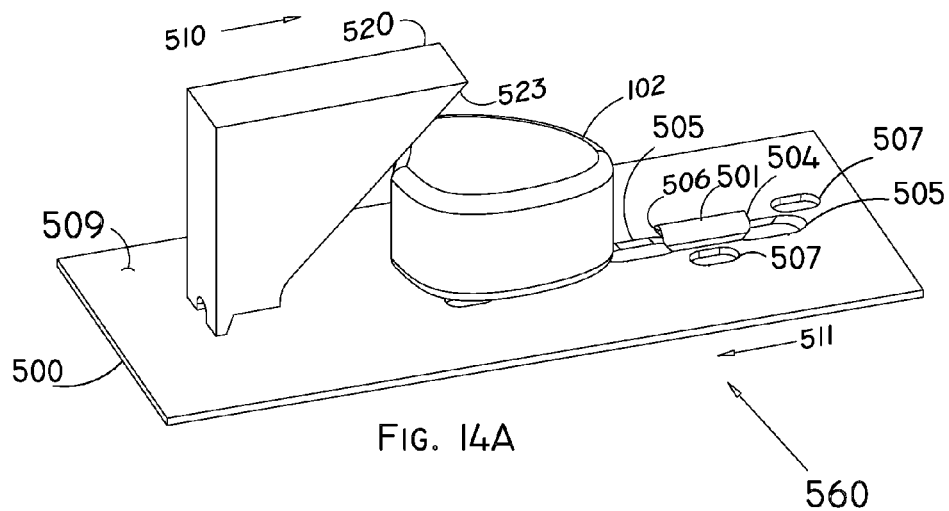
FIG. 14A is a perspective view of an embodiment of rasp system 560.

FIG. 14A is a perspective view of an embodiment of rasp system 560 comprising rasp 500 and trimming member 520. Rasp 500 and trimming member 520 may move relative to each other in the directions of 510 and 511 for milling material 102.

Rasp 500 may have at least one cutting tooth 501 that may protrude from the surrounding base surface 509 and may have one or more cutting faces 506 with cutting edges 504.

Figure 14B:
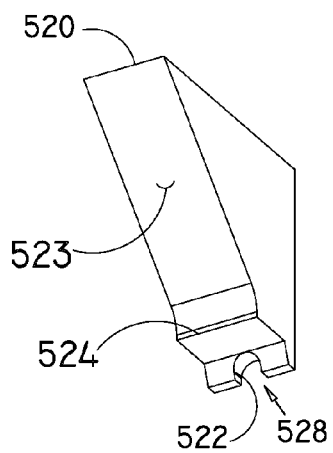
FIG. 14B is a perspective view of the trimming member 520.

FIG. 14B is a perspective view of the trimming member 520 that may include a push surface 523, leading trimming edge 524, and a trimming tooth 528 with trimming cutting edge 522.

Figure 14C:
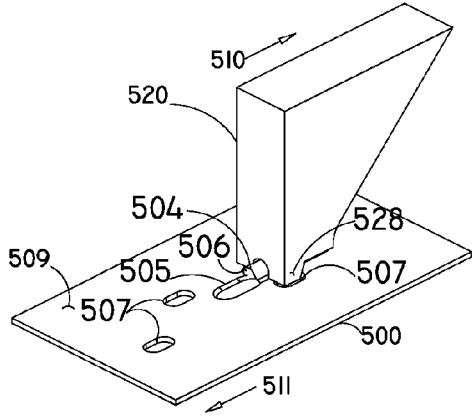
FIG. 14C is a perspective view of an embodiment of rasp system 560.

As shown, a pair of trimming ribs in combination may be considered a trimming tooth 528 with trimming cutting edge 522, which may approximately contour according to the tooth cutting edges 504 shown in FIG. 14C to enable a cutting or slicing interaction between the tooth cutting edges 504 and the trimming cutting edge 522.

FIG. 14C is a perspective view of embodiment of the rasp system 560 illustrating tooth cutting edge 504 and the trimming tooth 528 aligned respect to each other effecting cutting and trimming process as the trimming member 520 and rasp 500 move relative to each other in the directions of 510 and 511. The cut and trimmed portion of material 102 my pass through the aperture 505 which may have a size approximately equal to or larger than the face 506 of the cutting tooth 501; and the trimming tooth 528 may sweep the trimmed residuals into the apertures 507 that are located in the path of the trimming tooth 528. The apertures 507 may be in a path of travel of the trimming tooth 528. The particles that are larger than the sizes of the apertures 505 and 507 may remain on the surface 509 for receiving further cut-and-trim processing; only particles that are smaller than the sizes of the apertures 505 and 507 may pass through the rasp 500 for collection.

Generally, the sizes of the rasp cutting tooth 501 and apertures 505 and 507 may determine the sizes of the milled particles regardless of the hardness or density of material 102. As illustrated in FIGS. 14A-14C, a trimming tooth 528 is contoured (in other works, having a complementary or mating shape) for interfacing with the cutting tooth 501 to effect trimming of the material 102.

Figure 15A:
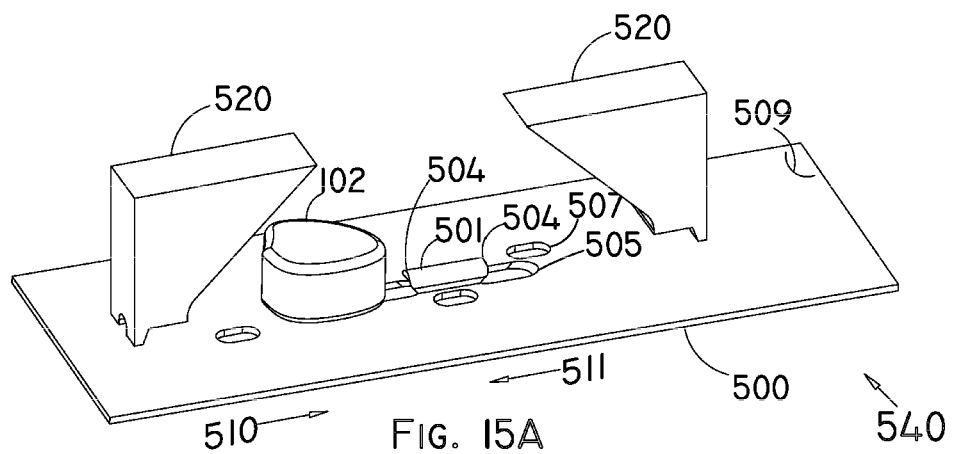
FIG. 15A is a perspective view of an embodiment of rasp system 540.

FIG. 15A is a perspective view of an embodiment of the rasp system 540 that may include rasp 500 and two trimming members 520. The rasp 500 includes a tooth 501 that may have two cutting edges 504 and apertures 505 and 507 described above accordingly. The trimming members 520 and the rasp 500 may move and reciprocate in the 510 and 511 directions respect to each other that may cause cutting and trimming portions of material 102 in both directions. In the case tooth 501 having one cutting edge 504 and the rasp 500 moving and the reciprocating directions 510 and 511, cutting tooth 501 may cut-and-trim a portion of material 102 in one direction and may instead agitate or tumble material 102 in the other direction.

Figure 15B:
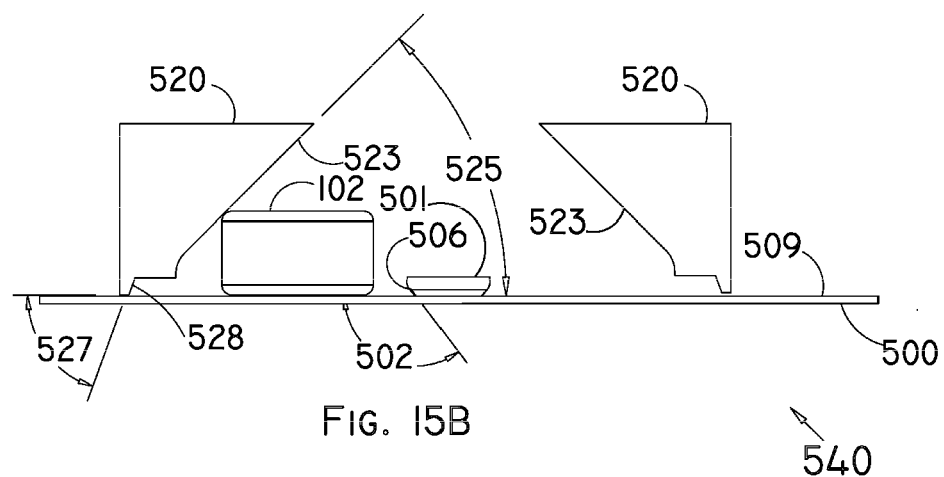
FIG. 15B is a side view of the rasp system 540 with tilt angles.

FIG. 15B is a side view of the rasp system 540 illustrating the associating tilt angles. As shown, faces 506 of the cutting tooth 501 may have a tilting angle 502 respect to the surface 509 of the rasp surface 509. The angle 502 may facilitate cutting portions of the material 102.

As shown in FIG. 15B, the push surface 523 of the trimming member 520 may have a tilting angle 525 respect to the surface 509 of the rasp. Furthermore, the cutting face of the trimming tooth 528, or trimming ribs 521, may also have a tilting angle 527 respects to the surface 509 of the rasp 500, which may generate additional downward force to eject the cut-and trimmed particle through the aperture 505 during the trimming process. Combinations of the cutting tooth angle 502 and the trimming tooth face angle 527 may generate a downward force on the cut portion of the material 102 during the trimming process, which may enhance self-clearing capability of rasp system 540.

Figure 15C:
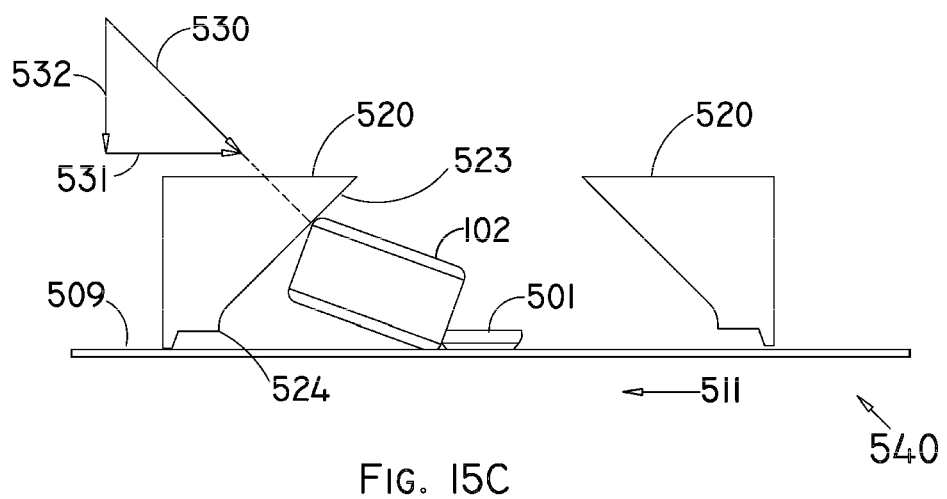
FIG. 15C is a side view of the rasp system 540 with milling forces.

FIG. 15C is a side view of the embodiment of rasp system 540 showing milling forces 531 and 532 caused by the tilt angle 525 of the push surface 523. The rasp 500 moving in the linear direction 511 may first cause the cutting tooth 501 and the push surface 523 of the trimming member 520 to engage material 102. Further movement of rasp 500 in the direction 511 may result in generating the cutting force 531 and the force 532 that may pushes material 102 toward the rasp surface 509. The rasp 500 moving further in the direction 511 may cause cutting and removing a portion of the material 102 with the rasp tooth 501 that may resemble a nibbling process. The rasp 500 moving even further in the direction of 511 may cause trimming the upper part of the nibbled portion with the combination of the cutting edges 504 of cutting tooth 501 and the leading trimming edge 524. The rasp 500 may continue moving in the direction 511 to complete the trimming process with the trimming tooth cutting edges 522 shown in FIG. 14B.

Accordingly, the instantaneous milling force may divide in three smaller milling forces. That is: 1) the force needed to initiate and promote the nibbling; 2) the force required to trim the upper part of the nibbled portion; and 3) the force needed to complete the trimming process with the cutting edges 522. Consequently, dividing the instantaneous milling force in smaller cutting and trimming forces may reduce the size of the required driving mechanical motor, which may contribute to reduction of the size and cost of the milling apparatus.

Figure 16A:
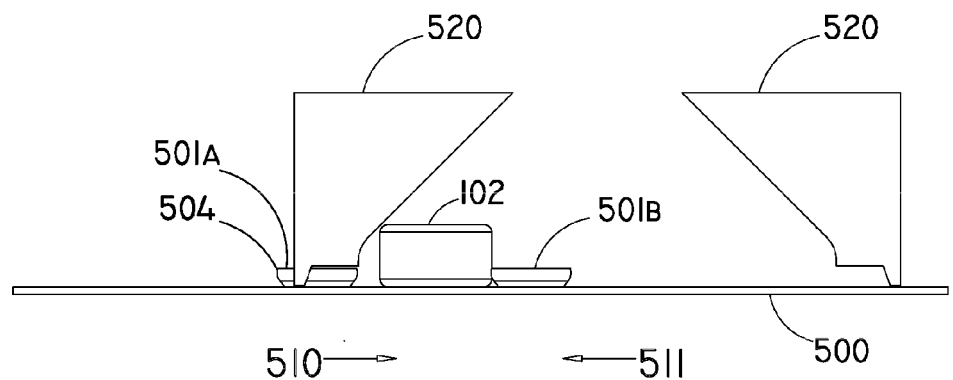
FIG. 16A is side view of an embodiment of rasp system 545.

FIG. 16A is a side view of an embodiment of rasp system 545 that may include rasp 500 with two rasp cutting teeth 501A and 501B, and two trimming members 520 that include two trimming teeth and the apertures 505 and 507 accordingly.

As shown in FIG. 16A, the instantaneous milling force of a rasp system with multiple cutting teeth may further reduce by allowing fewer or one cutting tooth at a time to engage material 102. As shown in FIG. 16A, cutting edge 504 of cutting tooth 501A may have passed all cutting edges of the trimming member 520 before cutting tooth 501B engaging material 102.

Figure 16B:
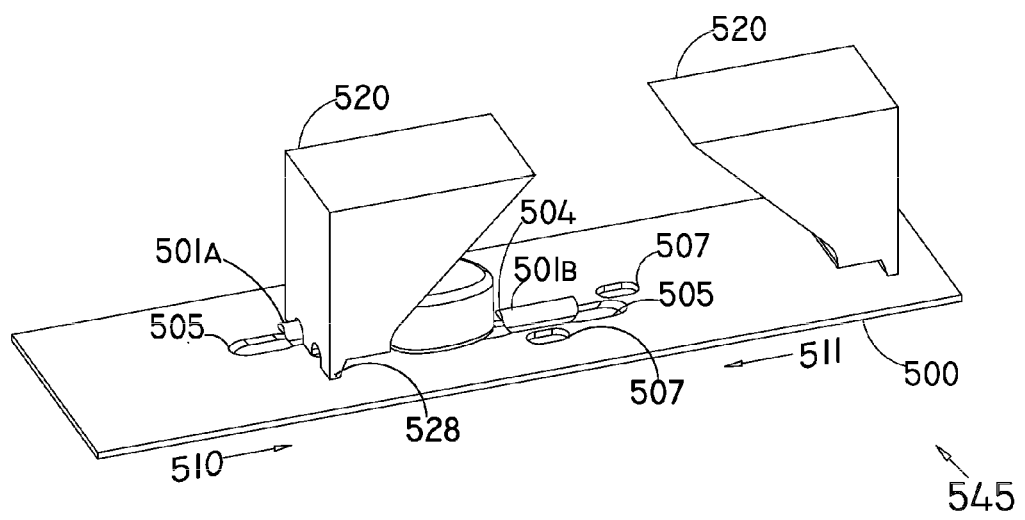
FIG. 16B is a perspective view of an embodiment of rasp system 545.

FIG. 16B is a perspective view of the embodiment of rasp system 545 showing lateral spacing between the cutting teeth 501A and 501B. As shown, the lateral spacing between the cutting tooth 501A and 501B may provide clear paths for the movements of trimming teeth 528, which may sweep the trimmed residuals into the apertures 507.

FIG. 17A is a perspective view of an embodiment of radial rasp system 1000 for automatic milling material 102. The radial rasp system 1000 that include a rotary trimming member, spindle 800 and a stationary rasp 900. A revolving hollow cylinder coupled to the outer flange 813, detailed not shown, or a rotating shaft coupled to the keyed pin 805 may drive spindle 800. Material 102 may feed into the spindle 800 opening 801 for milling and the spindle 800 may rotate or reciprocate rotation in the directions 802 for milling the material 102.

Figures 19A, 19B, 19C:
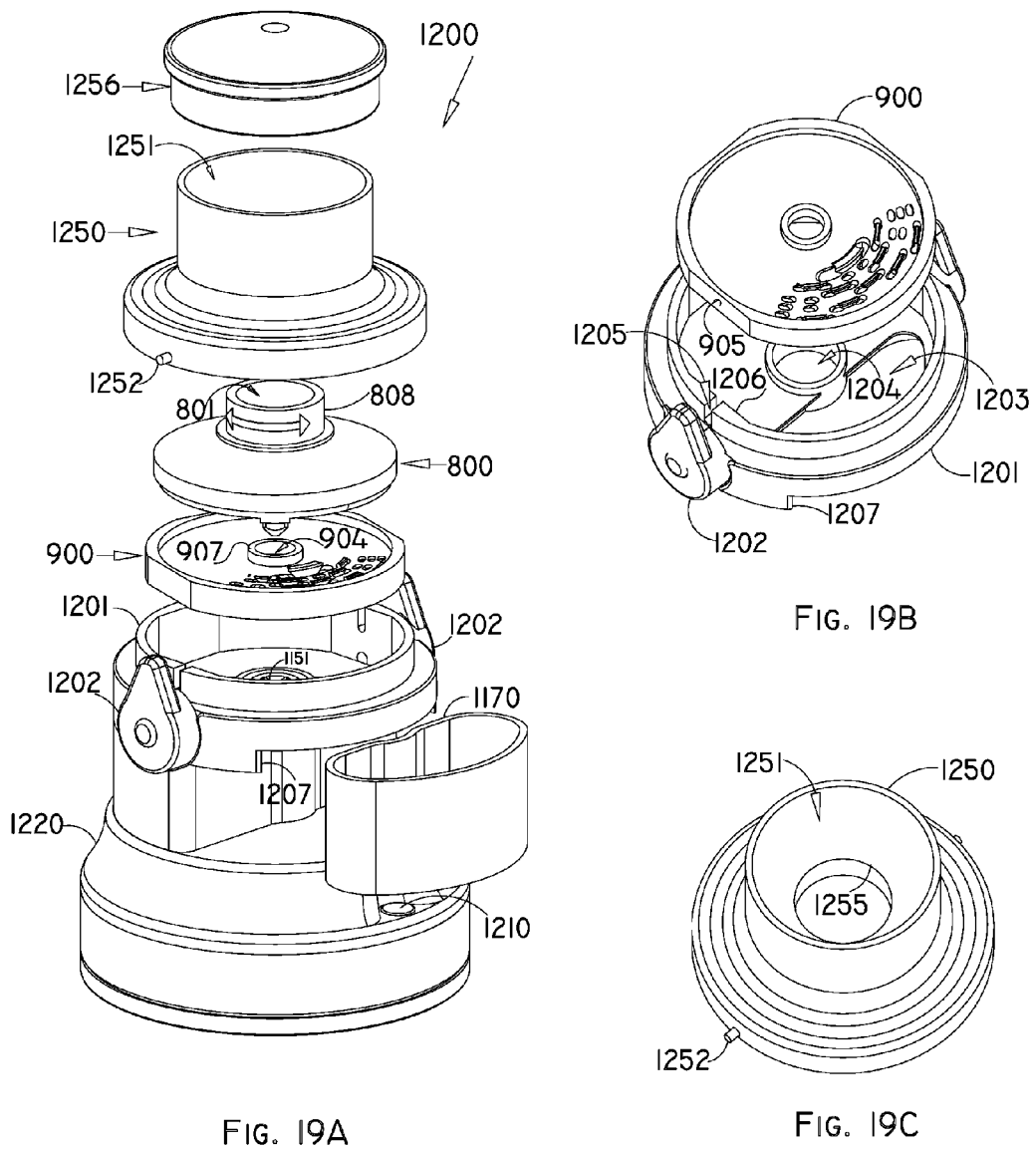
FIG. 19A is a perspective exploded view of an embodiment of a radial automatic milling apparatus 1200.
FIG. 19B is a perspective view of more detailed design of the embodiment of the ring 1201.
FIG. 19C is a perspective view of an embodiment of lid 1250.

Rasp 900 may include a keyed flange 905 disposed to couple to a stationary ring, for example ring 1200 shown in the embodiment in FIG. 19B.

FIG. 17B is a perspective view of an embodiment of a cross feeder 804 that may include arms 806, which may permanently affix to the spindle 800; and may include a centrally located keyed coupling pin 805 disposed for coupling to a rotating shaft for driving spindle 800.

FIG. 17C is a perspective view of the inside of the spindle 800. As shown, as an example, spindle 800 may include three ramped openings, radial channels 814 with inclined push surfaces 809 and sidewalls 811; cross feeder 804 with the keyed coupling pin 805; trimming teeth 809 that may have tilting face angle 807 conceptually similar to the angle 527 of the embodiment in FIG. 15B; and leading trimming edges 815. The sidewalls 811 may have less than approximately 90 degrees angle with respect to the surface 909 of the rasp 900, conceptually similar to the angle 525 in the embodiment in FIG. 15B.

To facilitate continual flow of the material 102 radially, caused by centrifugal forces, the sidewall 811, or a portion of one of the sidewall 811, may radially have a divergence angle 820.

FIG. 17D is a perspective view of the embodiment of the rasp 900, which may include multiple cutting teeth 901 and 906; and the cutting teeth may be of different sizes and may each have two cutting edges disclosed herein that may provide higher milled output when spindle 800 reciprocate rotation in directions 802, shown in FIG. 17A.

Figure 18:
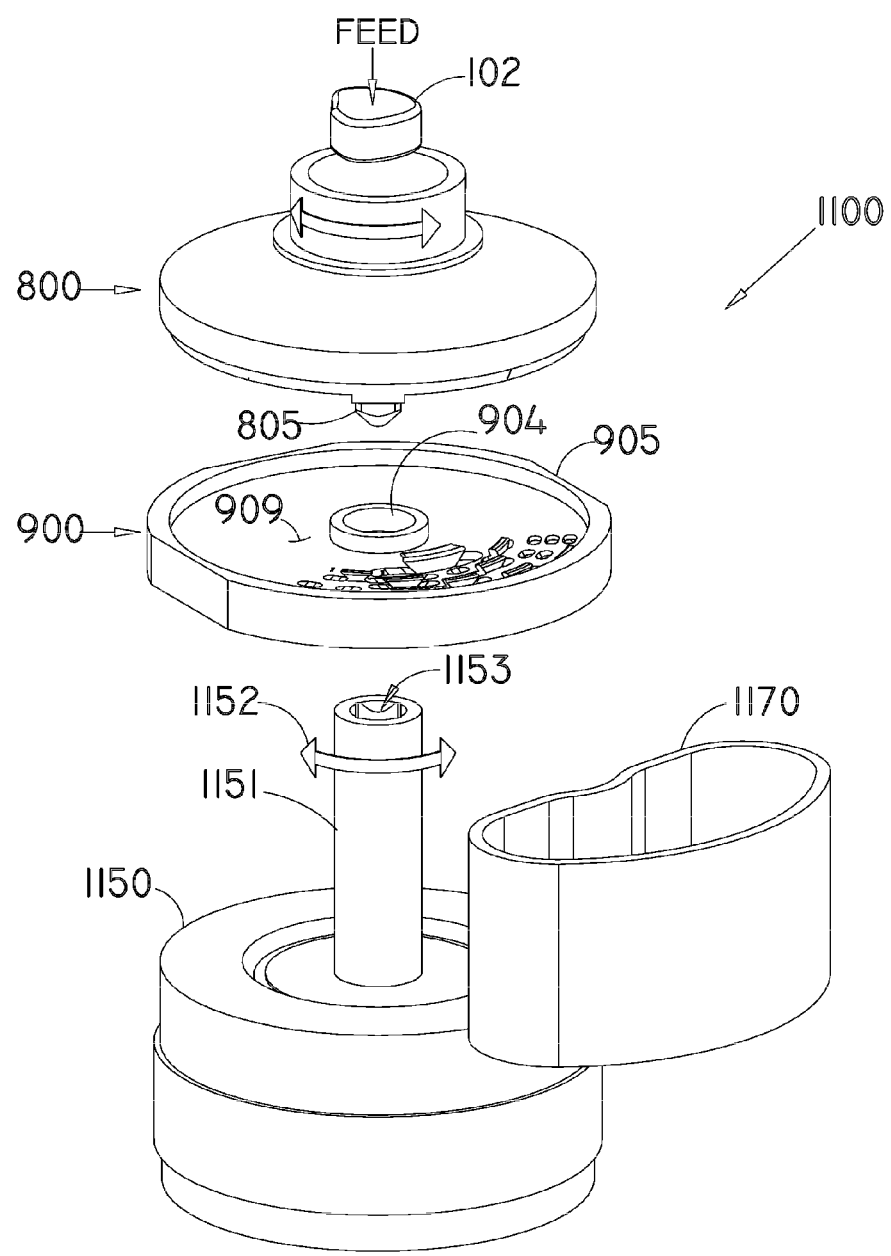
FIG. 18 is a perspective exploded view of embodiments of elements for automatic milling apparatus 1100 for milling material.

A portion of the rasp surface 909 may populate with the cutting teeth 901, 906 and apertures 903, 906 for accommodating for the convenient location and size of the container 1170 shown in FIG. 18. Rasp 900 may include a centrally located opening 904 disposed to allow coupling pin 805 to reach the coupling 1153 of the driving shaft 1151, shown in FIG. 18.

Figure 17E:
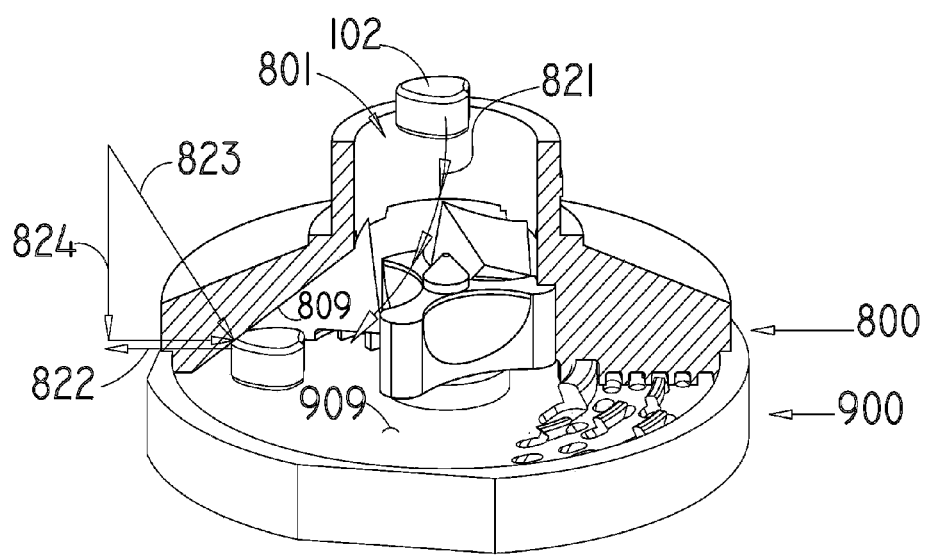
FIG. 17E is a perspective view of an embodiment of the rasp 900 and sectional view of spindle 800.

FIG. 17E is a perspective view of an embodiment of the rasp 900 and sectional view HH (shown in FIG. 17C) of spindle 800 joined to form the rasp system 1000. As shown, material 102 may enter the rotating spindle 800 via the spindle opening 801. The gravitational force may direct the material 102 downwardly and the rotational centrifugal force may direct material 102 radially. Material 102 may take the travel path 821 to enter the radial channel 814, arriving at the tapered surface 809; the material 102 may exert centrifugal force 822 on the tapered surface 809. The tapered surface 809 may in return exert force 823 on the material 102 causing a push force 824, which may push material 102 against the rasp surface 909; and at elevated spindle revolving speed, the push force 824 may be strong enough to cause the cut-and-trim milling process.

The mechanical force caused by the tilt angle of the sidewalls 811, conceptually similar to the force 532 in conjunction with the embodiment in FIG. 15C, may add to the centrifugal push force 824 to effect milling process at lower spindle 800 revolving speed.

The centrifugal push force 824 or combination of the mechanical force added to force 824 may eliminate the need for an operator to push material 102 against the rasp surface 909 of the rasp 900.

Having the rasp cutting teeth located on concentric paths and radially spaced from each other to provide clear concentric paths for the trimming teeth 809, after several rotations of the spindle 800 the rasp cutting teeth may cut circular grooves in the material 102, and may exhaust available material in the grooves to cut.

At nearly zero spindles 800 revolving speed materials 102 may become nearly free from the centrifugal force 822 allowing the cutting teeth of rasp 900 to function as agitators tumbling and reorienting material 102 in random directions. Consequently, reciprocating direction of rotation of spindle 800 may provide an automatic milling process comprising: 1) revolving spindle 800 at nominal speed for several rotations, cutting-and-trimming portions of material 102; 2) reversing rotation, or reducing spindle revolving speed, for agitating-disorientation of material 102; 3) repeating step 1 and 2 to continue automatic milling of material 102.

Rasp system 1000 may provide for automatic milling of material 102 to a predetermined particle-size distribution profile considering: 1) centrifugal push forces 824 eliminating the need for an operator for pushing material against the rasp; 2) divergence angle 820 facilitating flow of material 102 in the radial channels; 3) revolving spindle 800 in reciprocal directions for continual milling. As explained earlier in conjunction with the embodiment in FIG. 14C, the milled particle-sizes may primarily depend on the sizes of the rasp and trimming cutting teeth as well as the sizes of the apertures; and milled particle-sizes may not primarily depend on the hardness or density of material 102.

FIG. 18 is a perspective exploded view of embodiments of basic elements for automatic milling apparatus 1100 for milling material 102, utilizing the self-clearing rasp system 1000. The basic milling elements of the automatic milling apparatus 1100 may include revolving spindle 800, stationary rasp 900, motor 1150, and container 1170. Motor 1150 may include a rotating shaft 1151 that may rotate or reciprocate rotation in the directions 1152, and the shaft 1151 may include coupling 1153 disposed to couple to the driving coupling pin 805 of the spindle 800. The container 1170 may collect the milled particles and may support graft preparation and may include arrangements, not shown, for directly delivering the prepared graft to the surgical sight or may comprise an outlet, not shown, for the attachment of the delivery device. The size of the mouth of the container 1170 may be equal or larger than the active portion of surface 909 of rasp 900, populated with cutting teeth and the apertures, for efficient collection of milled particles.

The driving coupling pin 805 may pass through the opening 904 of the rasp 900 to couple to the coupling 1153 when the spindle 800 and the rasp 900 join.

FIG. 19A is a perspective exploded view of an embodiment of a radial automatic milling apparatus 1200 for milling material 102 to a predetermined particle-size distribution profile utilizing the basic milling elements of apparatus 1100 shown in FIG. 18.

The milling apparatus 1200 includes body 1220; container 1170; keyed stationary ring 1201 disposed to receive the rasp system 1000; lid 1250, which may cover the spindle 800 and provide a matching bearing surface for the spindle bearing 808; cap 1256 disposed to close the milling chamber; and switch 1210 for controlling the milling apparatus 1200. Ring 1201 may affix or may remove ably affix to the body 1220 of the milling apparatus 1200.

Body 1220 may house a frameless electric motor similar to the motor 1150 shown in FIG. 18, or other mechanical drivers such as a pneumatically driven mechanical motor. A battery or a separate electric power unit, not shown, may power the electric motor and may receive on-off signals from switch 1210.

For positioning container 1170 directly under the rasp 900, the container 1170 may slide in position guided by two rails 1207, detailed not shown. The stationary ring 1201 may receive rasp 900 matching keys 905 with keys 1206, shown in FIG. 19B.

Rasp 900 may include bearing surface 907 disposed to support the weight of the spindle 800 preventing trimming elements of spindle 800 touching surface or cutting elements of rasp 900. Lid 1250 may include two pins 1252 disposed to cooperate with the two latches 1202 disposed to latch down the lid 1250 for remove ably covering the spindle 800, details for the design of the latches not shown. Cap 1256 disposed to remove ably cover the lid 1250 limiting escape of material dust, i.e. bone dust, during the milling process.

FIG. 19B is a perspective view of more detailed design of the embodiment of the ring 1201. Ring 1201 may include an opening 1203, bearing and seal housing 1204 for the shaft 1151 shown in FIG. 18. Two grooves 1205 disposed to contain the lid pins 1252 preventing lid 1250 from rotation during milling operation; and three keys 1206 to match the keys 905 of rasp 900 preventing rasp 900 from rotation. Further, ring 1201 includes two latches 1202 rotate ably affixed to ring 1201; and ring 1201 may include a safety-interlocking switch disposed to prevent operating the mill without the lid 1250 latched down and secured in its position, details not shown.

Opening 1203 disposed to allow milled particles to drop into the container 1170, which may position directly under the rasp 900. The opening 1203 may be equal or larger than the active area of the rasp surface 909 for efficient collection of the milled particles.

FIG. 19C is a perspective view of the embodiment of lid 1250 that may include funneled opening 1251 for feeding material 102 into the opening 801 of the spindle 800, bearing 1255 matching spindle bearing 808, and two side pins 1252 disposed to cooperate with latches 1202 to latched down the lid 1250 during the milling process.

Figure 20:
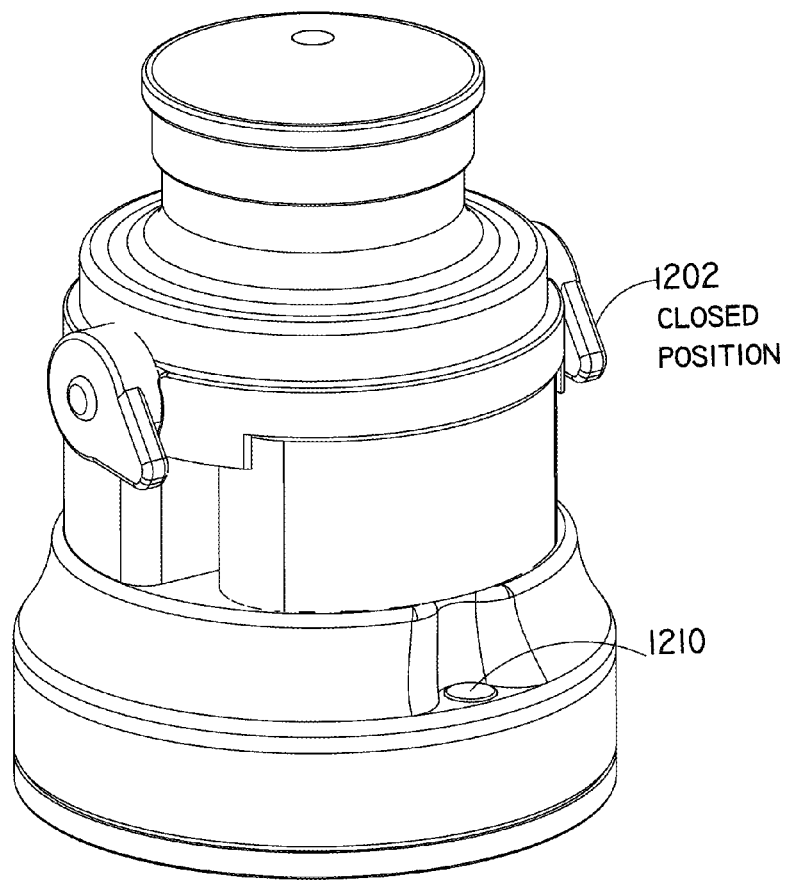
FIG. 20 is a perspective view of the fully assembled embodiment of automatic milling apparatus 1200.

To operate the apparatus 1200, operator may insert rasp 900 into the ring 1201; insert the spindle 800 in the rasp 900; insert container 1170 in the apparatus 1200; and place lid 1250 on the ring 1201 and rotate the latches 1202 to the closed position as shown in FIG. 20. Subsequently, operator may drop material 102 into the funnel 1251 of the lid 1250 and place the cap 1256 on the lid. Operator may now activate the switch 1210 to start the automatic milling process for milling material 102 to a predetermined particle-size distribution profile.

FIG. 20 is a perspective view of fully assembled embodiment of automatic milling apparatus 1200, with the latches 1202 in the closed position.

Figure 21A:
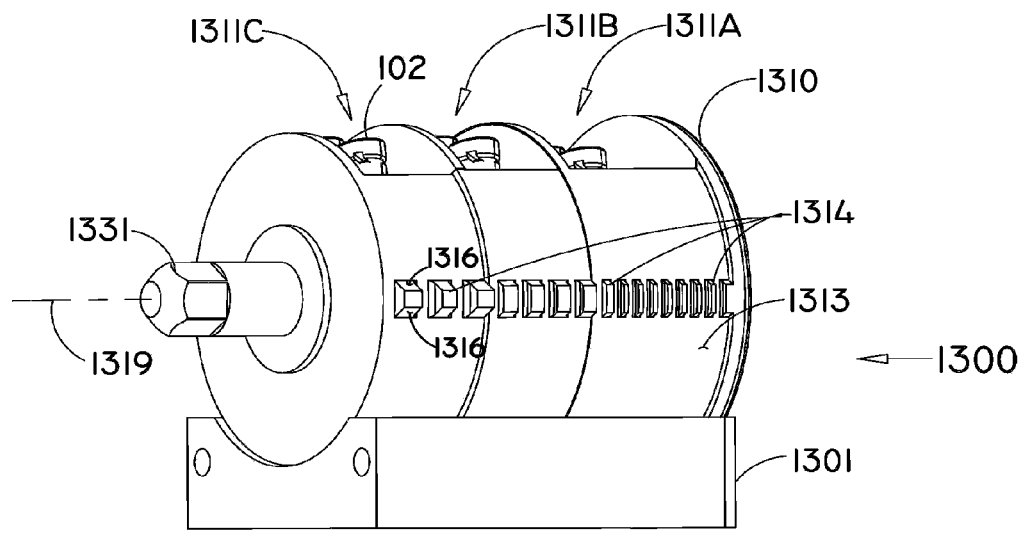
FIG. 21A is a perspective view of an embodiment of radial rasp system 1300.

FIG. 21A is a perspective view of an embodiment of radial rasp system 1300 comprising: a radial rasp 1301 and a radial trimming member 1310, which may include a keyed coupling 1331 disposed for coupling to a mechanical rotary device.

The radial trimming member 1310, rotor 1310, may include one or more than one individually partitioned radial channels, i.e. 1311A, 1311B, and 1311C disposed for receiving and containing material 102 for milling; and a surface 1313, that may include trimming teeth 1314 with tilted faces 1316 for enhancing self-clearing capability of the rasp system 1300. The trimming teeth 1314 may have different sizes; and each of the sizes may associate with each of the individually partitioned channels 1311A, 1311B, and 1311C. Rotor 1310 may rotate around the axis 1319.

Figure 21B:
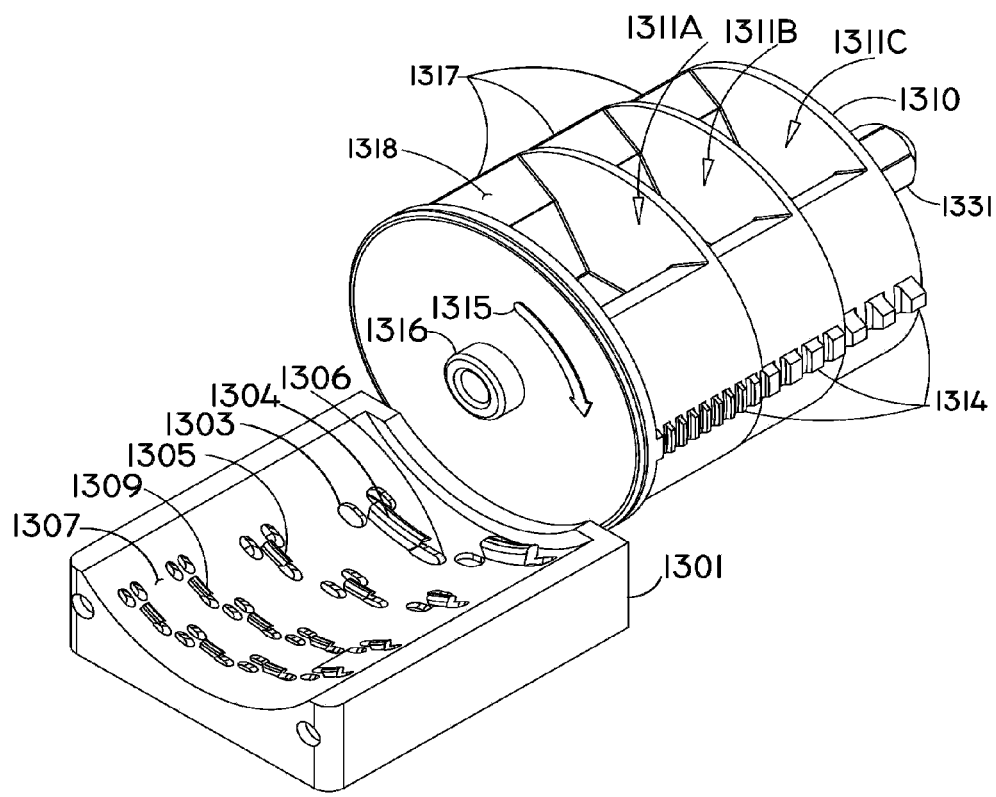
FIG. 21B is a perspective view of the embodiment of rasp 1301 separated from the rotor 1310.

FIG. 21B is a perspective view of embodiment of rasp 1301 separated from the rotor 1310. Rasp 1301 may have a curved surface 1307 that may match the outer curvature of the rotor 1310. The surface 1307 may include more than one cutting teeth, i.e. cutting teeth 1304, 1305, and 1309, and the cutting teeth may have different sizes and each of the sizes may associate with one of the individually partitioned radial channels for milling material 102. For examples, the largest cutting teeth 1304 may cut material 102 in channel 1311C, the smaller cutting teeth 1305 may cut material 102 in the radial channel 1311B, and the smallest cutting teeth 1309 may only cut material 102 in radial channel 1311A. Further, the surface 1307 may include multiple different sizes of apertures, i.e. 1303, 1306 associating with the different sizes of the cutting teeth, accordingly.

As shown in FIG. 21B, rotor 1310 may comprise leading trimming edges 1317 and push surfaces 1318 that may have a tilt angles, approximately less than 90-degree respects to the surface 1307 of rasp 1301, which may provided added mechanical milling force explained earlier in conjunction with the embodiments in FIG. 15B and FIG. 15C.

Multiple radial channels of rasp system 1300 associating with different sizes of the rasp cutting teeth may provide to surgeon ability to adjust the particle-size distribution profile for specific graft procedures. For example, in a case of hip or knee revision arthroplasty, with bone graft (morselized bone), the surgeon may repair damage joint surfaces, pits, holes, and other cavities as he discovers during the surgical procedure.

Accordingly, for example, the surgeon may increase the load of material 102 in the radial channel 1311C as compared with equal loadings of radial channels 1311A, 1311B, to increase the relative population of the larger size particles in the bone graft in favor of better biomechanics of the bone graft. In the case of small fillings and repairs, for example, the surgeon may increase the material 102 loading of partition 1311A and may reduce material 102 loading of partition 1311C in order to obtain a finer and more suitable bone graft for the task.

To achieve the desired change in the particle-size distribution profile as planned, it may require milling to completion all the materials 102 in the partitions, for example, 1311A, 1311B, and 1311C.

Figure 22A:
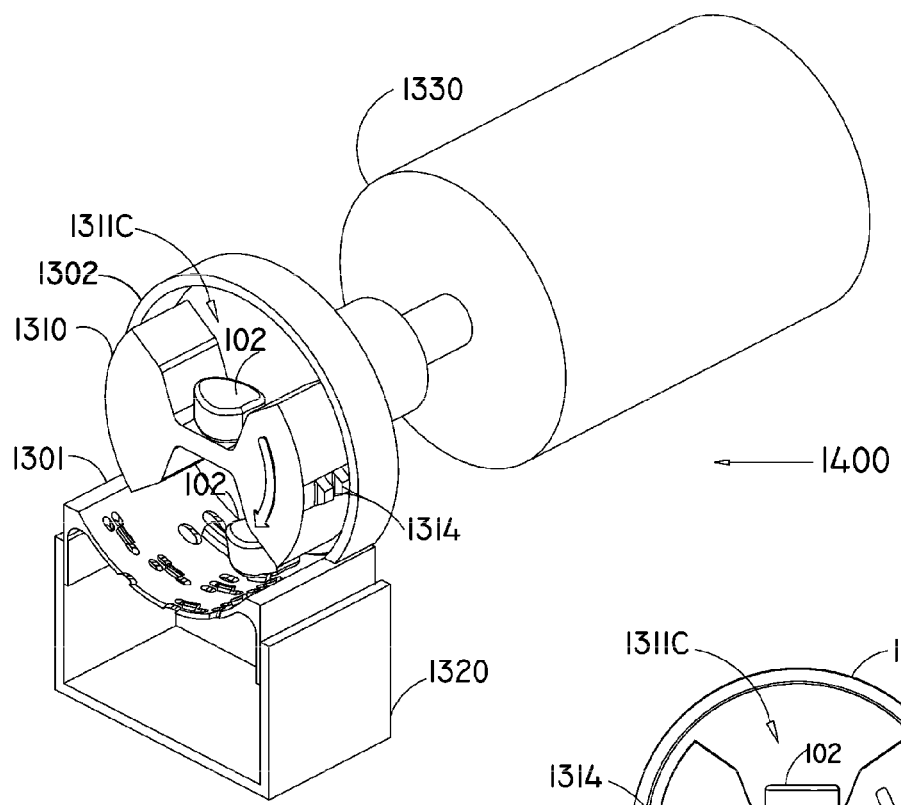
FIG. 22A is perspective cut away view of the basic milling elements of an embodiment of automatic milling apparatus 1400.

FIG. 22A is a perspective cut away view of the basic milling elements of an embodiment of apparatus 1400, for automatic milling material utilizing the rasp system 1300. The basic milling elements of apparatus 1400 may include rasp 1301; milling enclosure 1302; rotor 1310; container 1320; and motor 1330 disposed for driving rotor 1310.

Figure 22B:
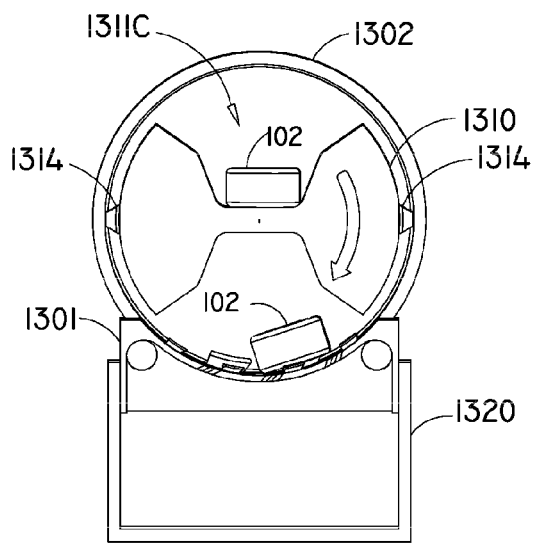
FIG. 22B is a front cut away view of the embodiment of apparatus 1400 at rest.

FIG. 22B is a front cut away view of the embodiment of apparatus 1400, showing rotor 1310 at rest, and channel 1311C loaded with materials 102 that rested on the bottom of channel 1311C and on the surface of rasp 1301.

Figure 23:
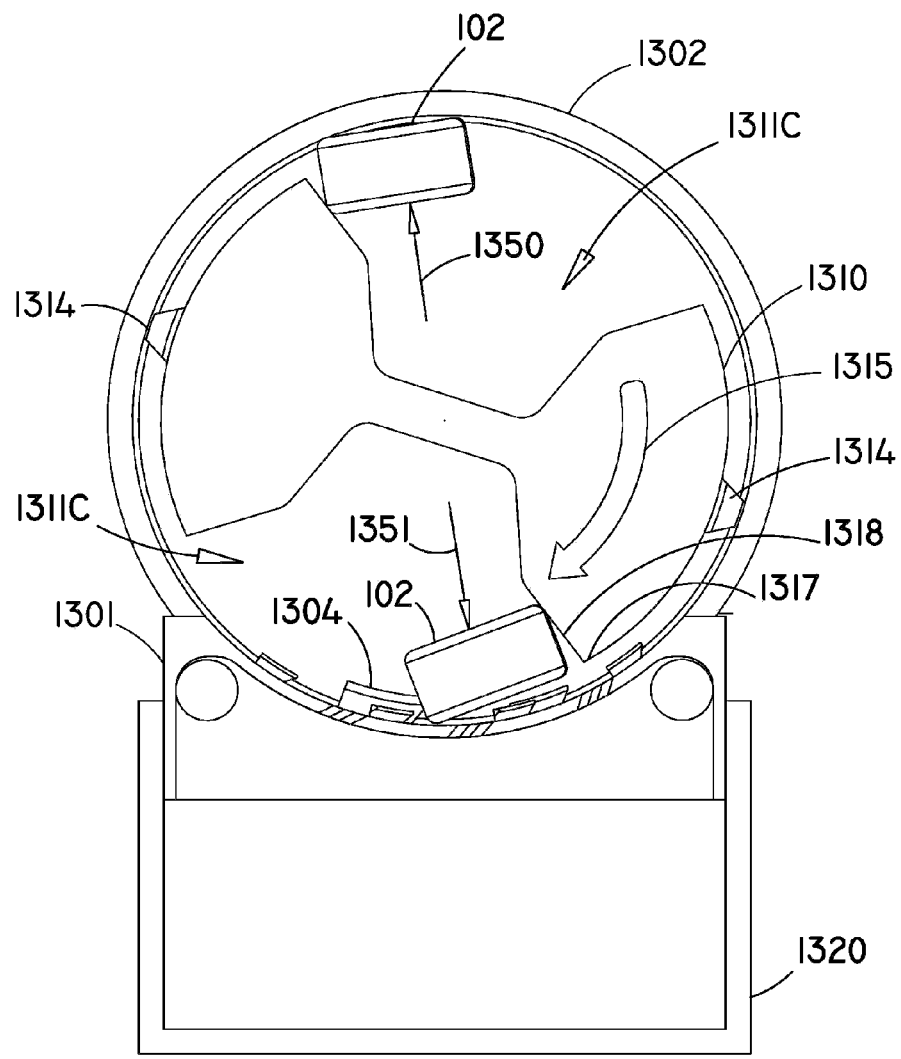
FIG. 23 is a front cut away view of the embodiment of apparatus 1400 milling material.

FIG. 23 is a front cut away view of embodiment of apparatus 1400 showing rotor 1310 revolving in the direction 1315 for milling materials 102.

The materials 102 trapped in the radial channel 1311C and rotating with the rotor 1310 experience centrifugal forces 1350 and 1351, which radially and directly force material 102 against the inner wall of milling enclosure 1302 and against the surface 1307 of the rasp 1301.

At elevated revolving speed of rotor 1310, material 102 may experience sufficiently strong centrifugal push force 1351; and rasp cutting tooth 1304 and the push surface 1318 may first engage material 102 and may first nibble a portion of the material 102. A push surface 1318 is operative to sweep material 102 over the surface 1307 of the rasp 1301. Subsequently, rotor 1310 continuing its rotation, leading edge 1317 and subsequently trimming tooth 1314 may complete the trimming process and the trimmed particle may fall into the container 1320 through aperture 1306, and the trimmed residuals may fall into the container 1320 through aperture 1303 of the rasp 1301, shown in FIG. 21B. The method disclosed herein utilizes centrifugal forces as direct push forces for pushing material 102 against the rasp surface 1307. This milling method may utilize to mill other materials requiring control of the particle-size distribution.

Having the rasp-cutting teeth located on concentric paths and spaced from each other along the axis of rotation 1319, shown in FIGS. 21A and 21B, after several rotations of rotor 1310, the rasp-cutting teeth, i.e. 1304, may cut arcuate grooves equal to its dimensions in the material 102 exhausting available material in the arcuate grooves to cut. At nearly zero rotor-revolving speed, the materials 102 may become nearly free from the centrifugal forces 1351, allowing the cutting teeth of rasp 1310 to function as agitators, tumbling and reorienting materials 102 in random directions.

In order to reorient the material 102 for continued milling process the revolving speed of rotor 1310 may reduce to provide the tumbling-reorienting process. Ramping revolving speed of rotor 1310 up and down may provide an automatic milling process comprising: 1) revolving rotor 1310 at nominal speed for several rotations for cutting-and-trimming material 102; 2) reducing rotor-revolving speed for agitating-reorienting of material 102; and 3) repeating steps 1 and 2 to continue automatic milling of material 102. For example, controlled pulsing with controlled angular acceleration-deceleration of the driving motor may accomplish continued automatic milling of material 102.

Figure 24A:
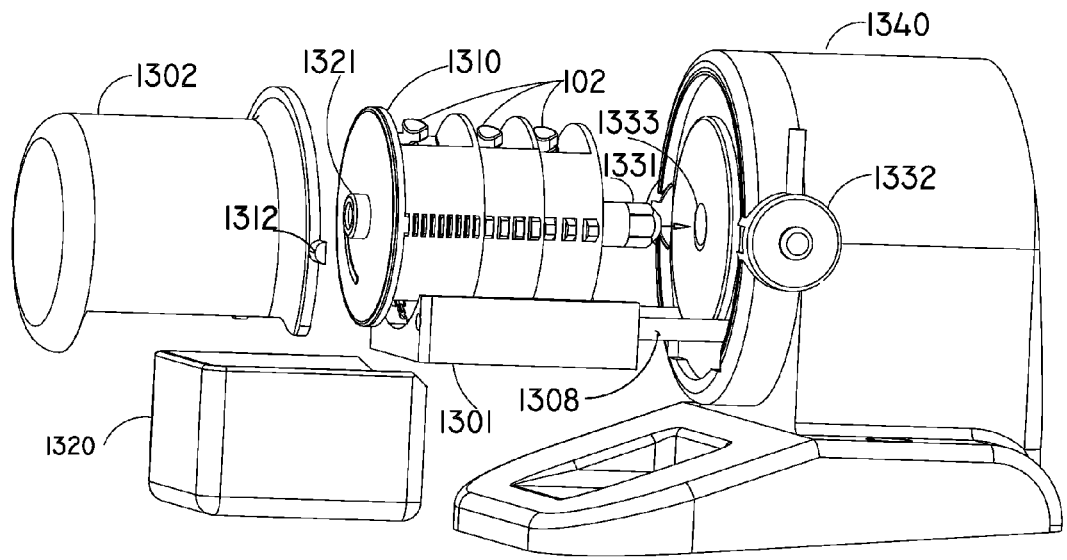
FIG. 24A is perspective view of exploded embodiment of automatic milling apparatus 1400.

FIG. 24A is a perspective view of exploded embodiment of apparatus 1400 for automatic milling of material 102 utilizing rasp system 1300. The body 1340 of apparatus 1400 may house a mechanical driving motor, for example, a frameless electric motor similar to the motor 1150 shown in FIG. 18 or other types of mechanical driving motors such as a pneumatic motor. Further, the body 1340 may include an opening 1333 disposed to allow coupling 1331 of the rotor 1310 to reach and couple to the coupling of the motor inside the frame 1340, detail not shown. Furthermore, body 1340 may include two latches 1332, one on each side, disposed to engage pins 1312 of milling enclosure 1302 for latching and securing the milling enclosure 1302 to the body 1340; two pins 1308 disposed for holding rasp 1301 in position; and a pair of switches 1319 for controlling the motor's electrical control and power unit, not shown. The body 1340 may house a removable battery for providing power to the motor.

Rotor 1310 may include a centrally located bearing arrangement 1321 disposed to loosely match a centrally locate bearing arrangement inside the milling enclosure 1302 for stabilizing the rotor 1310 when rotating, detail not shown.

To operate the apparatus 1400, operator may first install the rasp 1301 on the apparatus 1400, sliding the rasp 1301 over the two pins 1308 into its position. Then, operator may insert the coupling 1331 of the rotor 1310 into the opening 1333 of the body 1340; slide the container 1320 into the apparatus 1400; and load the radial channels 1311A, 1311B, and 1311C with the material 102. Finally, operator may attach the milling enclosure 1302 to the apparatus 1400 and close the two latches 1332. Operator may simultaneously activate two switches 1319, placed on each side of the mill, to start the automatic milling of material 102 for producing milled material, i.e., morselized bone having predetermined particle-size distribution profile.

Figure 24B:
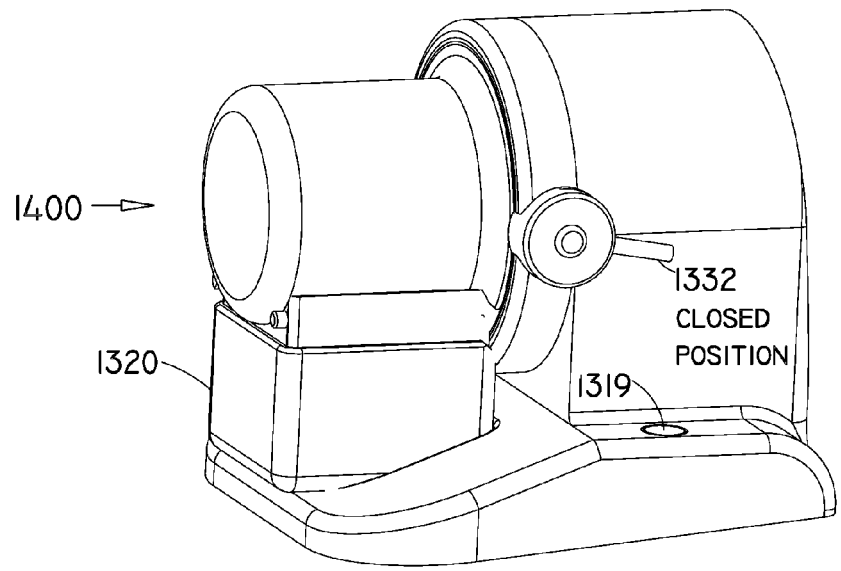
FIG. 24B is a perspective view of fully assembled embodiment of automatic milling apparatus 1400.

FIG. 24B is a perspective view of fully assembled of an embodiment of automatic milling apparatus 1400, with latch 1332 in closed position.

Upon completion of milling process, operator may stop apparatus 1400 by actuating either of the switches 1319 and subsequently slide the container 1320 away from the apparatus 1400 for preparation of bone graft. Operator may use container 1320 as a delivery device, arrangement not shown, or attaching a delivery device to the container 1320, detail not shown.

What is claimed is:

1. An apparatus for milling material to a predetermined particle size distribution profile, comprising:
    a base surface comprising:
        a first cutting tooth raised from a surrounding surface for cutting the material; and
        a first aperture in the surrounding surface of a predetermined size disposed adjacent the first cutting tooth so that material of less than the predetermined size may pass through the first aperture;
    a trimming member comprising:
        a first trimming tooth contoured for interfacing with the first cutting tooth to effect trimming of the material; and
    wherein the base surface and the trimming member are operable to move longitudinally relative to each other and to interface to trim and cut material when placed on the base surface during the relative movement of the base surface and the trimming member.

2. The apparatus of claim 1, wherein the base surface further comprises a second cutting tooth and a second aperture disposed adjacent to the second cutting tooth, further comprising a second trimming tooth contoured for interfacing with the second cutting tooth to effect the cutting and trimming of the material.

3. The apparatus of claim 2, wherein the first cutting tooth and the second cutting tooth are laterally offset from each other.

4. An apparatus for milling material to within a predetermined particle size distribution profile, comprising:
- a base surface comprising:
  - a first cutting tooth for cutting the material; and
  - a first aperture of a predetermined size disposed adjacent the first cutting tooth so that material of less than the predetermined size may pass through the first aperture;
- a trimming member comprising:
  - a first trimming tooth contoured for interfacing with the first cutting tooth to effect trimming of the material; and
- a push surface operative to sweep the material over the base surface as the material is moved and pushed against the base surface by centrifugal force in a radial direction during relative movement of the base surface and the trimming member;
- wherein the base surface and the trimming member are operable to move rotationally relative to each other and to interface to trim and cut material when placed on the base surface during the relative movement of the base surface and the trimming member.

5. The apparatus of claim 4, wherein the base surface further comprises a second cutting tooth and a second aperture disposed adjacent to the second cutting tooth, and further comprising a second trimming tooth contoured for interfacing with the second cutting tooth to effect the cutting and trimming of the material.

6. The apparatus of claim 5, wherein the first cutting tooth and the second cutting tooth are laterally offset from each other.

7. The apparatus of claim 6, wherein the first cutting tooth and the second cutting tooth are different sizes such that the material is milled to fit a predetermined particle size distribution profile.

8. The apparatus of claim 5, wherein the first cutting tooth comprises a first inclined face, and the second cutting tooth comprises a second inclined face.

9. The apparatus of claim 4, further comprising a container for collecting material passing through the apertures during milling.

10. The apparatus of claim 8, wherein the first aperture is disposed adjacent the first inclined face and wherein an angle between the first inclined face and the base surface is less than about ninety degrees.

11. The apparatus of claim 10, wherein the first and second apertures are arcuately aligned with the first and the second inclined faces, respectively.

12. The apparatus of claim 10, further comprising a drive mechanism for moving the base surface and trimming member relative to each other and for rotating a mixer paddle to mix the material.

13. An apparatus for milling material to a predetermined particle size distribution profile, comprising:
- a base surface comprising:
  - a first cutting tooth raised from a surrounding surface for cutting the material; and
  - a first aperture in the surrounding surface of a predetermined size disposed adjacent the first cutting tooth so that material of less than the predetermined size may pass through the first aperture;
- a trimming member comprising:
  - a first trimming tooth contoured for interfacing with the first cutting tooth to effect trimming of the material; and
- wherein the base surface and the trimming member are operable to move rotationally relative to each other and to interface to trim and cut material when placed on the base surface during the relative movement of the base surface and the trimming member.

* * * * *